US007809441B2

(12) United States Patent
Kane et al.

(10) Patent No.: US 7,809,441 B2
(45) Date of Patent: Oct. 5, 2010

(54) IMPLANTABLE MEDICAL DEVICE WITH CHEMICAL SENSOR AND RELATED METHODS

(75) Inventors: Michael John Kane, Lake Elmo, MN (US); Jeffrey Allen Von Arx, Minneapolis, MN (US); James Gregory Bentsen, North St. Paul, MN (US); Jonathan Kwok, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 611 days.

(21) Appl. No.: 11/383,933

(22) Filed: May 17, 2006

(65) Prior Publication Data

US 2007/0270675 A1 Nov. 22, 2007

(51) Int. Cl.
*A61N 1/08* (2006.01)
*A61N 1/365* (2006.01)
*A61B 5/1459* (2006.01)

(52) U.S. Cl. .......................... 607/22; 600/322; 600/348

(58) Field of Classification Search ..................... 607/2, 607/22, 62, 17, 25, 28; 600/310, 322, 333, 600/348

See application file for complete search history.

(56) References Cited

U.S. PATENT DOCUMENTS 4,200,110 A 4/1980 Peterson et al.
4,321,057 A 3/1982 Buckles
4,344,438 A 8/1982 Schultz et al.
4,399,099 A 8/1983 Buckles
4,680,268 A 7/1987 Clark
4,704,029 A 11/1987 Van Heuvelen
4,721,677 A 1/1988 Clark
4,750,494 A 6/1988 King (Continued)

FOREIGN PATENT DOCUMENTS

WO WO9625978 8/1996

(Continued)

OTHER PUBLICATIONS

"Microminiature Device Monitors Vital Electrolytes and Metabolites", *John Glenn Biomedical Engineering Consortium* NASA Glenn Research Center, Cleveland, OH May 2002, 2 pages.

(Continued)

*Primary Examiner*—Carl H. Layno
*Assistant Examiner*—Tammie K Heller
(74) *Attorney, Agent, or Firm*—Pauly, Devries Smith & Deffner, L.L.C.

(57) ABSTRACT

In an embodiment, the invention includes an implantable medical device with a pulse generator and a chemical sensor in communication with the pulse generator, the chemical sensor configured to detect an ion concentration in a bodily fluid. In an embodiment, the invention includes a method for providing cardiac arrhythmia therapy to a patient including sensing a physiological concentration of an analyte, communicating data regarding the physiological concentration of the analyte to an implanted pulse generator, and delivering therapy to the patient based in part on the physiological concentration of the ion. In an embodiment, the invention includes a method for monitoring diuretic therapy. In an embodiment, the invention includes a method for controlling delivery of an active agent into a human body. Other aspects and embodiments are provided herein.

28 Claims, 7 Drawing Sheets

U.S. PATENT DOCUMENTS 4,750,495 A 6/1988 Moore et al.
4,890,621 A 1/1990 Hakky
4,903,701 A 2/1990 Moore
4,981,779 A 1/1991 Wagner
5,001,054 A 3/1991 Wagner
5,040,533 A 8/1991 Fearnot
5,209,231 A 5/1993 Cote et al.
5,267,151 A 11/1993 Ham et al.
5,275,171 A 1/1994 Barcel
5,312,454 A 5/1994 Roline et al.
5,330,718 A 7/1994 Hui et al.
5,333,609 A 8/1994 Bedingham et al.
5,342,406 A 8/1994 Thompson
5,342,789 A 8/1994 Chick et al.
5,378,432 A 1/1995 Bankert et al.
5,457,535 A 10/1995 Schmidtke et al.
5,553,616 A 9/1996 Ham et al.
5,556,421 A 9/1996 Prutchi et al.
5,560,356 A 10/1996 Peyman
5,605,152 A 2/1997 Slate et al.
5,728,281 A 3/1998 Holmstrom et al.
5,830,138 A 11/1998 Wilson
5,854,078 A 12/1998 Asher
5,871,442 A 2/1999 Madarasz et al.
5,902,326 A 5/1999 Lessar et al.
5,958,782 A 9/1999 Bentsen et al.
5,995,860 A 11/1999 Sun et al.
6,002,954 A 12/1999 Van Antwerp et al.
6,011,984 A 1/2000 Van Antwerp et al.
6,040,194 A 3/2000 Chick et al.
6,049,727 A 4/2000 Crothall
6,122,536 A 9/2000 Sun et al.
6,125,290 A 9/2000 Miesel
6,125,291 A 9/2000 Miesel et al.
6,134,459 A 10/2000 Roberts et al.
6,144,866 A 11/2000 Miesel et al.
6,163,714 A 12/2000 Stanley et al.
6,187,599 B1 2/2001 Asher et al.
6,216,022 B1 4/2001 Tyrrell et al.
6,219,137 B1 4/2001 Vo-Dinh
6,232,130 B1 5/2001 Wolf
6,236,870 B1 5/2001 Madarasz et al.
6,256,522 B1 7/2001 Schultz
6,267,724 B1 7/2001 Taylor et al.
6,268,161 B1 7/2001 Han et al.
6,277,627 B1 8/2001 Hellinga
6,304,766 B1 10/2001 Colvin, Jr.
6,330,464 B1 12/2001 Colvin et al.
6,368,274 B1 4/2002 Van Antwerp et al.
6,383,767 B1 5/2002 Polak
6,438,397 B1 8/2002 Bosquet et al.
6,442,409 B1 8/2002 Peyman
6,454,710 B1 9/2002 Ballerstadt et al.
6,491,639 B1 12/2002 Turcott
6,505,059 B1 1/2003 Kollias et al.
6,521,446 B2 2/2003 Hellinga
6,544,800 B2 4/2003 Asher
6,579,690 B1 6/2003 Bonnecaze et al.
6,594,510 B2 7/2003 Madarasz et al.
6,625,479 B1 9/2003 Weber et al.
6,666,821 B2 12/2003 Keimel
6,671,527 B2 12/2003 Petersson et al.
6,673,596 B1 1/2004 Sayler et al.
6,682,938 B1 1/2004 Satcher, Jr. et al.
6,694,158 B2 2/2004 Polak
6,711,423 B2 3/2004 Colvin
6,731,976 B2 5/2004 Penn et al.
RE38,525 E 6/2004 Stanley et al.
6,766,183 B2 7/2004 Walsh et al.
6,771,993 B2 8/2004 Rule et al.
6,800,451 B2 10/2004 Daniloff et al.
6,804,544 B2 10/2004 Van Antwerp et al.
6,835,553 B2 12/2004 Han et al.
6,855,556 B2 2/2005 Amiss et al.
6,885,881 B2 4/2005 Leonhardt
6,885,883 B2 4/2005 Parris et al.
6,893,545 B2 5/2005 Gotoh et al.
6,918,873 B1 7/2005 Millar et al.
6,928,325 B2 8/2005 Zhu et al.
6,944,488 B2 9/2005 Roberts
6,952,603 B2 10/2005 Gerber et al.
6,957,094 B2 10/2005 Chance et al.
7,016,714 B2 3/2006 Colvin, Jr., et al.
7,039,446 B2 5/2006 Ruchti et al.
7,107,086 B2 9/2006 Reihl et al.
7,133,710 B2 11/2006 Acosta et al.
7,134,999 B2 11/2006 Brauker et al.
7,164,948 B2 * 1/2007 Struble et al. ................ 607/22
7,447,533 B1 11/2008 Fang et al.
7,450,980 B2 11/2008 Kawanishi
2002/0016535 A1 2/2002 Martin et al.
2002/0033454 A1 3/2002 Cheng et al.
2002/0035317 A1 3/2002 Cheng et al.
2002/0095075 A1 7/2002 Madarasz et al.
2002/0127626 A1 9/2002 Daniloff et al.
2003/0100040 A1 5/2003 Bonnecaze et al.
2003/0191376 A1 10/2003 Samuels et al.
2003/0208113 A1 11/2003 Mault et al.
2004/0023317 A1 2/2004 Motamedi et al.
2004/0030365 A1 2/2004 Rubin
2004/0059206 A1 3/2004 Braig et al.
2004/0073100 A1 4/2004 Ballerstadt et al.
2004/0087842 A1 5/2004 Lakowicz et al.
2004/0100376 A1 5/2004 Lye et al.
2004/0132172 A1 7/2004 Cunningham et al.
2004/0133079 A1 7/2004 Mazar et al.
2004/0147034 A1 7/2004 Gore et al.
2004/0161853 A1 8/2004 Yang et al.
2004/0180379 A1 9/2004 Van Duyne et al.
2004/0180391 A1 9/2004 Gratzl et al.
2004/0186359 A1 9/2004 Beaudoin et al.
2004/0199062 A1 10/2004 Petersson et al.
2004/0206916 A1 10/2004 Colvin, Jr. et al.
2004/0215134 A1 10/2004 Soykan et al.
2004/0249311 A1 12/2004 Haar et al.
2004/0254438 A1 12/2004 Chuck et al.
2004/0260162 A1 12/2004 Rohleder et al.
2005/0027176 A1 2/2005 Xie
2005/0033133 A1 2/2005 Kraft
2005/0038329 A1 2/2005 Morris et al.
2005/0042704 A1 2/2005 Alarcon et al.
2005/0043894 A1 * 2/2005 Fernandez .................. 702/19
2005/0065464 A1 3/2005 Talbot et al.
2005/0065556 A1 3/2005 Reghabi et al.
2005/0070768 A1 3/2005 Zhu et al.
2005/0070770 A1 3/2005 Dirac et al.
2005/0070771 A1 3/2005 Rule et al.
2005/0113657 A1 5/2005 Alarcon et al.
2005/0113658 A1 5/2005 Jacobson et al.
2005/0130249 A1 6/2005 Parris et al.
2005/0137481 A1 6/2005 Sheard et al.
2005/0148832 A1 7/2005 Reghabi et al.
2005/0154272 A1 7/2005 Dirac et al.
2005/0221276 A1 10/2005 Rozakis et al.
2006/0025748 A1 2/2006 Ye
2006/0217771 A1 9/2006 Soykan et al.
2007/0027495 A1 2/2007 Gerber
2007/0270674 A1 11/2007 Kane et al.
2007/0270675 A1 11/2007 Kane et al.

FOREIGN PATENT DOCUMENTS

WO WO9719188 5/1997
WO WO9801071 1/1998

| | | |
|---|---|---|
| WO | WO9902651 | 1/1999 |
| WO | WO 00/25863 | 5/2000 |
| WO | WO-0025862 | 5/2000 |
| WO | WO0180728 | 11/2001 |
| WO | WO2004039265 | 5/2004 |
| WO | WO2004071291 | 8/2004 |
| WO | WO-2004/081522 | 9/2004 |
| WO | WO2004091719 | 10/2004 |
| WO | WO2004092713 | 10/2004 |
| WO | WO2005074612 | 8/2005 |
| WO | WO-2006/017169 | 2/2006 |

OTHER PUBLICATIONS

"Microminiature Monitor for Vital Electrolyte and Metabolite Levels of Astronauts—Status Report", *John Glenn Biomedical Engineering Consortium* NASA Glenn Research Cener at Lewis Field, Apr. 2003, 5 pages.

Bakker, Eric et al., "Carrier-Based Ion-Selective Electrodes and Bulk Optodes. 1. General Characteristics", *Chem. Rev. 1997*, pp. 3083-3132.

Benco, John S. et al., "Optical Sensors for Blood Analytes", *The Spectrum*, vol. 14, Issue 4 Winter 2001, pp. 4-11.

Bender, J. W. et al., "The Use of Biomedical Sensors to Monitor Capsule Formation Around Soft Tissue Implants", *Annals of Plastic Surgery*, vol. 56, No. 1 Jan. 2006, pp. 72-75.

Buhlmann, Philippe et al., "Carrier-Based Ion-Selective Electrodes and Bulk Optodes. 2. Ionophores for Potentiometric and Optical Sensors", *Chem. Rev*. 1998, 1953-1687.

Han, In S. et al., "Constant-Volume Hydrogel Osmometer: A New Device Concept for Miniature Biosensors", *Biomacromolecules*, 3 2002 , pp. 1271-1275.

He, Huarui et al., "Enantioselective Optodes", *Analytica Chimica Acta*, 246 1991 , pp. 251-257.

Kuwana, Eddy et al., "Sensing of pH in Multiply Scattering Media with Fluorescence Lifetime", *Advanced Biomedical and Clinical Diagnostic Systems, Proceedings of SPIE*, vol. 4958, 2003, pp. 32-42.

Lehn, J. M. et al., "[2]-Cryptates: Stability and Selectivity of Alkali and Akaline-Earth Macrobicycle Complexes", *Journal of the American Chemical Society* Nov. 12, 1975, pp. 6700-6707.

Tohda, Koji et al., "A Microscopic, Continuous, Optical Monitor for Interstitial Electrolytes and Glucose", *Chemphyschem 2003*, pp. 155-160.

Tohda, Koji et al., "Micro-miniature Autonomous Optical Sensor Array for Monitoring Ions and Metabolites 1: Design, Fabrication, and Data Analysis", *Analytical Sciences*. vol. 22 Mar. 2006 , pp. 383-388.

Tsai, HC et al., "Simultaneous Determination of Renal Clinical Analytes in Serum using Hydrolase- and Oxidase-Encapsulated Optical Array Biosensors", *Analytical Biochemistry 334* 2004 , pp. 183-192.

Voskerician, Gabriela et al., "Biocompatibility and Biofouling of MEMs Drug Delivery Devices", *Biomaterials 24* 2003 , pp. 1959-1967.

EP Communication mailed Mar. 24, 2009 in co-pending EP patent application No. 07762189.4, "*Implantable Medical Device with Chemical Sensor and Related Methods*", (13 pages).

"PCT International Search Report and Written Opinion from International Application No. PCT/US2007/068954, mailed Oct. 31, 2007, pp. 1-16".

EP Response filed Jul. 27, 2009 to Communication dated Mar. 24, 2009 in co-pending EP patent application no. 07762189.4, "Implantable Medical Device with Chemical Sensor and Related Methods", (9 pages).

File History of U.S. Appl. No. 11/383,926, filed May 17, 2006 (747 pages).

EP Office Action mailed Mar. 16, 2010 in co-pending EP patent application No. 07762189.4, "Implantable Medical Device with Chemical Sensor and Related Methods", (3 pages).

Office Action mailed Mar. 26, 2010 in co-pending U.S. Appl. No. 11/383,926, filed May 17, 2006 (10 pages).

* cited by examiner

IMPLANTABLE MEDICAL DEVICE WITH CHEMICAL SENSOR AND RELATED METHODS

TECHNICAL FIELD

This disclosure relates generally to implantable medical devices and, more particularly, to implantable medical devices with a chemical sensor and related methods.

BACKGROUND OF THE INVENTION

Implantable medical devices (IMDs), such as cardiac rhythm management systems, are commonly used to provide treatment or therapy to patients. Cardiac rhythm management systems can include pacemakers. Pacemakers deliver timed sequences of low energy electrical stimuli, called pacing pulses, to the heart, via an intravascular lead wire or catheter (referred to as a "lead") having one or more electrodes disposed in or about the heart. Heart contractions are initiated in response to such pacing pulses. Pacemakers are often used to treat patients with bradyarrhythmias, that is, hearts that beat too slowly, or irregularly. Such pacemakers may also coordinate atrial and ventricular contractions to improve pumping efficiency.

Cardiac rhythm management systems can also include cardiac resynchronization therapy (CRT) devices for coordinating the spatial nature of heart depolarizations for improving pumping efficiency. For example, a CRT device may deliver appropriately timed pacing pulses to different locations of the same heart chamber to better coordinate the contraction of that heart chamber, or the CRT device may deliver appropriately timed pacing pulses to different heart chambers to improve the manner in which these different heart chambers contract together.

Cardiac rhythm management systems also include defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, that is, hearts that beat too quickly. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac rhythm management systems can also include devices that combine these functions, as well as monitors, drug delivery devices, and other implantable or external systems or devices for diagnosing or treating the heart.

Certain physiological analytes impact many of the problems that implantable medical devices are designed to treat. As one example, potassium ion concentrations can affect a patient's cardiac rhythm. Therefore, medical professionals frequently evaluate physiological potassium ion concentration when diagnosing a cardiac rhythm problem. However, measuring physiological concentrations of analytes, such as potassium, generally requires drawing blood from the patient. Blood draws are commonly done at a medical clinic or hospital and therefore generally require the patient to physically visit a medical facility. As a result, despite their significance, physiological analyte concentrations are frequently measured only sporadically.

SUMMARY OF THE INVENTION

Disclosed herein, among other things, is an implantable medical device (IMD) for sensing chemical concentration in a bodily fluid. In an embodiment, the invention includes an implantable medical device with a pulse generator and a chemical sensor in communication with the pulse generator, the chemical sensor configured to detect an ion concentration in a bodily fluid. The chemical sensor can include a sensing element, an optical excitation assembly, and an optical detection assembly.

In an embodiment, the invention includes an implantable cardiac rhythm management system having a pulse generator and a chemical sensor in communication with the pulse generator, the chemical sensor configured to detect an ion concentration in a bodily fluid. The chemical sensor can include a sensing element, an optical excitation assembly, and an optical detection assembly.

In an embodiment, the invention includes a method for providing cardiac arrhythmia therapy to a patient. The method can include optically measuring a physiological concentration of an ion in a bodily fluid of the patient with an implanted chemical sensor. The method can further include transmitting data regarding the physiological concentration of the ion to an implanted pulse generator. The method can also include delivering therapy from the implanted pulse generator to the patient based in part on the physiological concentration of the ion.

In an embodiment, the invention includes a method of monitoring diuretic therapy. The method can include optically sensing a physiological concentration of an ion in a bodily fluid of the patient with an implanted chemical sensor. The method can also include communicating data regarding the physiological concentration of the ion to an implanted pulse generator. The method can further include altering the delivery of the diuretic therapy to the patient based in part on the physiological concentration of the ion.

In an embodiment, the invention includes a method for controlling delivery of an active agent into a human body. The method can include measuring a physiological concentration of one or more analytes with an implanted system comprising a pulse generator and a chemical sensor, the chemical sensor comprising a sensing element, an excitation assembly, and a detection assembly. The method can further include varying delivery of the substance at least in part as a function of the measured concentration of the one or more analytes.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION OF THE INVENTION

Figure 1:
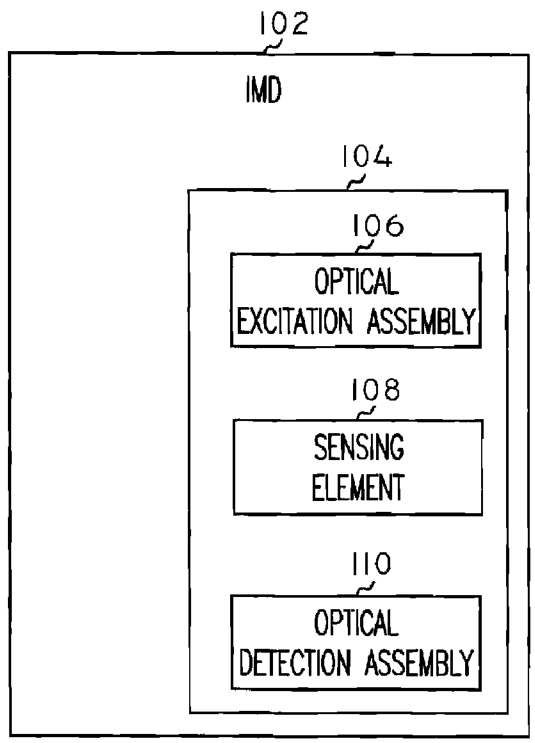
FIG. 1 schematically illustrates aspects of an implantable medical device (IMD) with a chemical sensor in accordance with an embodiment of the invention.

The disclosures of commonly-owned U.S. Pat. No. 7,225,024, filed on Sep. 30, 2003, and U.S. Publication No. 2004-0133079, filed on Jan. 2, 2003, are herein incorporated by reference.

Physiological analyte concentrations are important data points for both the diagnosis and treatment of many medical problems. For example, knowledge of potassium ion concentrations can be important to the correct diagnosis of cardiac arrhythmias. The excitation cycle of cardiac cells is influenced by their resting electrical potential, and by the activity of ion channels (such as potassium, sodium, and calcium) in the cell membrane of the cardiac cells. By way of example, potassium ion channels play an important role in returning a cardiac cell to a resting electrical potential following an action potential. When the concentration of potassium in the plasma is within a normal physiological range, the potassium ion channels can function effectively. Unfortunately, when the potassium concentration in the plasma is elevated ("hyperkalemia") the concentration gradient of potassium across the cardiac cell membrane is reduced and the cardiac cell generally becomes depolarized and inexcitable. In contrast, when the potassium concentration is low ("hypokalemia"), the concentration gradient of potassium across the cardiac cell membrane is increased resulting in hyperpolarization of the resting electrical potential. Hypokalemia can lead to arrhythmias, such as atrial fibrillation. Thus, knowledge of potassium ion concentrations can be valuable in forming a correct diagnosis of a cardiac rhythm problem. Likewise, the concentrations of other physiological ions, such as sodium and calcium, can also be important in the diagnosis and treatment of cardiac arrhythmias.

Beyond cardiac rhythm problems, ion sensing can also be useful in the context of monitoring drug therapy, monitoring renal function, titrating drugs (such as hearth failure medications), monitoring for heart failure decompensation, and observing primary electrolyte imbalance subsequent to dietary intake or renal excretion variations.

Embodiments of the present invention can be used to gather concentration data regarding medically relevant analytes in bodily fluids. Specifically, embodiments of the present invention can include an implantable medical device including a pulse generator to deliver electrical pulses and/or shock therapy and a chemical sensor in communication with the pulse generator. The chemical sensor can be configured to detect an ion concentration in a bodily fluid, and can include a sensing element, an excitation assembly, and a detection assembly configured to receive light from the sensing element.

Integrating the functionality of chemical sensors with implantable cardiac rhythm management devices can offer therapeutic advantages. The data generated by an implantable cardiac rhythm device and the data generated by a chemical sensor offer mutually orthogonal but linked views of the physiologic state of the patient. Combining these views can provide a health professional with additional insight into the patient's health. As just one example, an erratic heart-rate in the presence of very high or very low potassium concentrations indicates a greater level of risk to the patient than either condition presented separately. Various embodiments of the present invention can detect both analyte concentrations, such as potassium concentration, and cardiac arrhythmias so that risks can be quickly identified and, in some embodiments, conveyed to a health professional when appropriate.

Continuous or near-continuous monitoring of physiological analytes can offer therapeutic benefits. Typically, the process for measuring physiological concentrations of analytes involves drawing blood from the patient. Blood draws are typically done at a medical clinic or hospital. Therefore, the patient must generally visit a medical facility, and as a result, physiological analyte concentrations are generally measured only sporadically. Accordingly, the clinician is usually presented with only sporadic snapshot data representing a patient's condition only on particular days. While this snapshot data is valuable, having data stretching over a longer continuous period of time can be of greater value because it can more accurately reflect trends as well as periodic fluctuations that could be caused by diet, activity, medications, etc. Various embodiments of the invention, including an implantable medical device with a chemical sensor, can be used to provide clinicians with continuous or semi-continuous data regarding analyte concentrations.

When a medical device is implanted within a host, the immune system of the host senses the presence of the foreign body and starts what is referred to as a foreign body response. Within hours, there is adherence and activation of platelets in the area of the inserted device, followed by the release of growth factors and chemotactic agents from platelet granules. Granulocytes and mononuclear phagocytes then migrate into the area. Subsequently, the site is infiltrated by fibroblasts. Within the first few weeks, the fibroblasts multiply and lay down collagen that begins to form an avascular connective tissue envelope or "pocket". This process can continue for months and generally results in the complete encasement of the medical device in an avascular pocket with walls that are 50 μm to 200 μm thick.

Unfortunately, chronically implanted medical devices with chemical sensors can suffer from problems as a result of the foreign body response. The pocket wall itself is poorly vascularized and serves to prevent the medical device from interfacing with highly vascularized tissues. Without interfacing with highly vascularized tissues, the medical device may not be able to accurately detect physiological conditions outside of the pocket. As an example, glucose is known to traverse the pocket wall relatively poorly and therefore glucose levels within the pocket do not accurately reflect physiological glucose levels outside of the pocket. Therefore most implanted glucose sensors become increasingly inaccurate as the avascular pocket forms around them. However, as detailed in Example 1 below, the Applicants have discovered that ions, such as sodium and potassium ions, behave differently than glucose in traversing the pocket wall. Specifically, Example 1 shows that ions such as sodium and potassium are able to traverse the pocket wall sufficiently well to enable accurate measurements regarding their physiological concentrations to be taken from within the pocket wall. Therefore, chemical sensors that detect physiological ions, such as sodium and potassium, can be integrated with chronically implanted medical devices, such as implantable cardiac rhythm management devices.

Closely related to the issues associated with the foreign body response are issues associated with biofouling of implanted medical devices. Biofouling can include the accumulation of biomolecules such as proteins, fats, and/or carbohydrates on the surfaces of an implanted device. While not intending to be bound by theory, biofouling is believed to lead to drift and loss of responsiveness in the context of electrochemical (such as potentiometric) chemical sensors that are implanted chronically. For ion selective electrodes, the measured electromotive force primarily depends on the potential change across the interface of the sample and membrane phases. This interfacial measured electromotive force can become compromised by the deposition of proteins and other biomolecules on the sensor surface. Furthermore, in ion-selective electrodes, the bulk of the sensor membrane is generally impregnated with a known excess of an analyte. The Nernstian response is only observed if the organic phase boundary concentration is not significantly altered as a function of the sample concentration. For acute measurements, this condition is maintained. However, for chronic monitoring, preloaded analyte can leach from the sensor film, compromising calibration.

In contrast, both non-carrier and carrier based optical sensing elements rely on concentration changes within the bulk of the sensing element. Therefore, optical sensing approaches are believed to be generally less susceptible to biofouling problems than electrochemical chemical sensors relying on interfacial phenomena.

It will be appreciated that the sensing of analyte concentrations can be directed at a specific analyte or a plurality of different analytes. In an embodiment, the analyte sensed is one or more analytes relevant to cardiac health. In an embodiment, the analyte sensed is one or more analytes indicative of renal health. The analyte sensed can be an ion or a non-ion. The analyte sensed can be a cation or an anion. Specific examples of analytes that can be sensed include acetic acid (acetate), aconitic acid (aconitate), ammonium, blood urea nitrogen (BUN), B-type natriuretic peptide (BNP), bromate, calcium, carbon dioxide, cardiac specific troponin, chloride, choline, citric acid (citrate), cortisol, copper, creatinine, creatinine kinase, fluoride, formic acid (formate), glucose, hydronium ion, isocitrate, lactic acid (lactate), lithium, magnesium, maleic acid (maleate), malonic acid (malonate), myoglobin, nitrate, nitric-oxide, oxalic acid (oxalate), oxygen, phosphate, phthalate, potassium, pyruvic acid (pyruvate), selenite, sodium, sulfate, urea, uric acid, and zinc. Inorganic cations sensed by this method include but not limited to hydronium ion, lithium ion, sodium ion, potassium ion, magnesium ion, calcium ion, silver ion, zinc ion, mercury ion, lead ion and ammonium ion. Inorganic anions sensed by this method include but not limited to carbonate anion, nitrate anion, sulfite anion, chloride anion and iodide anion. Organic cations sensed by this method include but are not limited to norephedrine, ephedrine, amphetamine, procaine, prilocaine, lidocaine, bupivacaine, lignocaine, creatinine and protamine. Organic anions sensed by this method include but not limited to salicylate, phthalate, maleate, and heparin. Neutral analytes sensed by this method include but not limited to ammonia, ethanol, and organic amines. In an embodiment, ions that can be sensed include potassium, sodium, chloride, calcium, and hydronium (pH). In a particular embodiment, concentrations of both sodium and potassium are measured. In another embodiment, concentrations of both magnesium and potassium are measured.

In some embodiments, the physiological concentration of an analyte is sensed directly. In other embodiments, the physiological concentration of an analyte is sensed indirectly. By way of example, a metabolite of a particular analyte can be sensed instead of the particular analyte itself. In other embodiments, an analyte can be chemically converted into another form in order to make the process of detection easier. By way of example, an enzyme can be used to convert an analyte into another compound which is easier to detect. For example, the hydrolysis of creatinine into ammonia and N-methylhydantoin can be catalyzed by creatinine deiminase and the resulting ammonia can be detected by a chemical sensor. As another example, the oxidation of glucose into gluconolactone and hydrogen peroxide can be catalyzed by glucose oxidase and the resulting hydrogen peroxide can be detected by a chemical sensor. In some embodiments, the enzyme is immobilized to prevent it from leaching out of the chemical sensor.

Referring now to FIG. 1, a schematic view of an implantable medical device (IMD) 102 with a chemical sensor 104 is shown. In various embodiments, the IMD 102 can include a cardiac rhythm management device, such as a pacemaker, a cardiac resynchronization therapy (CRT) device, a remodeling control therapy (RCT) device, a cardioverter/defibrillator, or a pacemaker-cardioverter/defibrillator. One exemplary cardiac rhythm management device is disclosed in commonly assigned U.S. Pat. No. 6,928,325, issued Aug. 9, 2005, the contents of which is herein incorporated by reference. In the embodiment shown in FIG. 1, the chemical sensor 104 is integrated with the IMD 102. The chemical sensor 104 is configured to detect a concentration of an analyte, such as an ion, in a bodily fluid. Bodily fluids can include blood, interstitial fluid, serum, lymph, and serous fluid. The chemical sensor 104 includes a sensing element 108. The chemical sensor 104 also includes an excitation assembly 106 and a detection assembly 110. The chemical sensor 104 can be configured to operate in various ways including calorimetrically and/or fluorimetrically.

It will be appreciated that chemical sensors can be configured to operate in various other ways. For example, optical chemical sensors can be configured to directly illuminate tissues or fluids of the body and then analyze the resulting spectral response to determine analyte concentrations (e.g., a direct spectroscopic approach). However, while not intending to be bound by theory, it believed that such direct spectroscopic approaches generally suffer from issues that can impair accuracy including background interference and/or temporal signal drift associated with biofouling.

The excitation assembly 106 can be configured to illuminate the sensing element 108. In an embodiment, the excitation assembly 106 includes a light-emitting diode (LED). In some embodiments, the excitation assembly includes solid state light sources such as GaAs, GaAlAs, GaAlAsP, GaAlP, GaAsP, GaP, GaN, InGaAlP, InGaN, ZnSe, or SiC light emitting diodes or laser diodes that excite the sensing element(s) at or near the wavelength of maximum absorption for a time sufficient to emit a return signal. In other embodiments, the excitation assembly can include other light emitting components including incandescent components. In some embodiments, the excitation assembly 106 can include a waveguide. The excitation assembly 106 can also include one or more bandpass filters and/or focusing optics.

In some embodiments, the excitation assembly includes a plurality of LEDs with bandpass filters, each of the LED-filter combinations emitting at a different center frequency. According to various embodiments, the LEDs operate at different center-frequencies, sequentially turning on and off during a measurement, illuminating the sensing element. As multiple different center-frequency measurements are made sequentially, a single unfiltered detector can be used.

The sensing element 108 can include one or more ion selective sensors. Physiological analytes of interest can diffuse into the sensing element 108 and bind with an ion selective sensor to result in a fluorimetric or calorimetric response. Exemplary ion selective sensors are described more fully below.

The detection assembly 110 can be configured to receive light from the sensing element 108. In an embodiment, the detection assembly 110 includes a component to receive light. By way of example, in some embodiments, the detection assembly 110 includes a charge-coupled device (CCD). In other embodiments, the detection assembly can include a photodiode, a junction field effect transistor (JFET) type optical sensor, or a complementary metal-oxide semiconductor (CMOS) type optical sensor. In an embodiment, the detection assembly 110 includes an array of optical sensing components. In some embodiments, the detection assembly 110 can include a waveguide. The detection assembly 110 can also include one or more bandpass filters and/or focusing optics. In an embodiment, the detection assembly 110 includes one or more photodiode detectors, each with an optical bandpass filter tuned to a specific wavelength range.

The excitation and detection assemblies can be integrated using bifurcated fiber-optics that direct excitation light from a light source to one or more sensing elements, or simultaneously to sensing elements and a reference channel. Return fibers can direct emission signals from the sensing element(s) and reference channels to one or more optical detectors for analysis by a processor. In another embodiment, the excitation and detection assemblies are integrated using a beam-splitter assembly and focusing optical lenses that direct excitation light from a light source to the sensing element and direct emitted or reflected light from the sensing element to an optical detector for analysis by a processor.

In some embodiments, the detection assembly 110 is disposed on the same side of the sensing element 108 as the excitation assembly 106. In other embodiments, the detection assembly 110 is on the opposite side of the sensing element 108 from the excitation assembly 106. It will be appreciated that many different physical arrangements of the components are possible.

Embodiments of the invention can include an implantable medical device having a chemical sensor co-located with a pulse generator body, located on a lead connected to a pulse generator body through a header, or separately located in a sensor module in wired or wireless communication with a pulse generator body.

Figure 2:
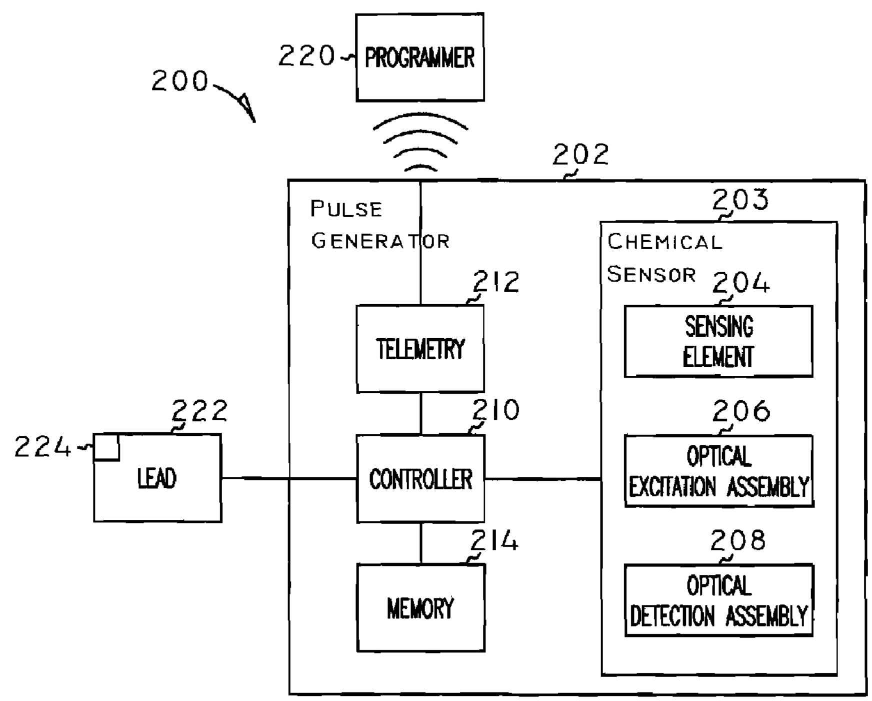
FIG. 2 schematically illustrates an IMD with a chemical sensor in accordance with another embodiment of the invention.

FIG. 2 schematically illustrates an implantable system 200 having a pulse generator 202 co-located with an integrated chemical sensor 203, according to various embodiments. The term "pulse generator" as used herein shall refer to the part or parts of an implanted system, such as a cardiac rhythm management system or a neurological therapy system, containing the power source and circuitry for delivering pacing and/or shock therapy. The pulse generator 202 can include a controller circuit 210 (including components such as a pulse generator circuit) to communicate with the chemical sensor 203, a telemetry circuit 212 to communicate with the controller circuit 210 and an external module 220 (such as a programmer module), and a memory circuit 214 to communicate with the controller circuit 210. The chemical sensor 203 includes a sensing element 204, an optical excitation assembly 206, and an optical detection assembly 208. The implantable system 200 can include at least one implantable lead 222 coupled to the pulse generator 202 via the controller circuit 210 (or pulse generator circuit), the at least one implantable lead 222 configured to be connected to at least one implantable electrode 224 capable of electrically stimulating tissue. However, it will be appreciated that embodiments of the invention can also include implantable systems, such as cardiac rhythm management systems, that do not include pacing leads, such as leadless implantable cardioverter-defibrillators.

In various embodiments, the controller circuit, telemetry circuit, and memory circuit are within a device body or housing. In some embodiments, the chemical sensor 203, or some of the components thereof, are disposed within the device body or housing. In some embodiments, the chemical sensor 203, or some of the components thereof are disposed on the device body or in an aperture in the device body. In an alternative embodiment, the optical excitation assembly 206 and the optical detection assembly 208 can be disposed within the device body, while the sensing element 204 is disposed outside of the device body. In such an embodiment, optical communication between the optical excitation assembly 206, the sensing element 204, and the optical detection assembly 208 is maintained by waveguides, optical lenses, or optical windows. For example, an optical lens or an optical window (transparent member) can be disposed within an aperture on the device body, the sensing element can be optically coupled to the outside of the lens or window, and the optical excitation assembly and optical detection assembly can be optically coupled to the inside of the lens or window.

Figure 3:
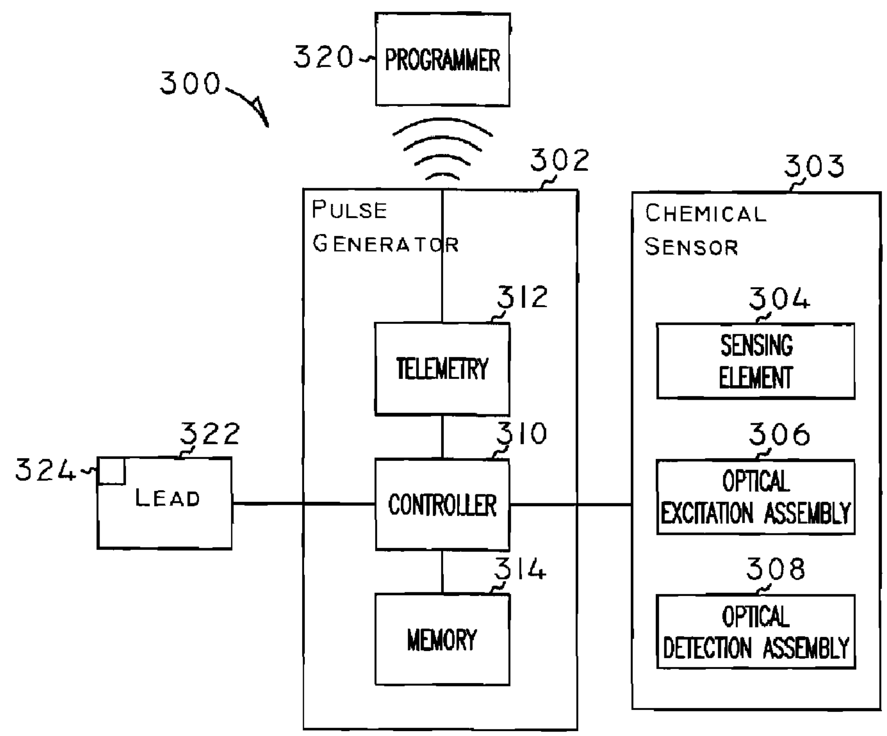
FIG. 3 schematically illustrates an IMD with a chemical sensor in accordance with another embodiment of the invention.

FIG. 3 illustrates an embodiment of an implantable system 300 having a pulse generator 302 coupled to (such as electrically or optically), but separate from, a chemical sensor 303. The pulse generator 302 can include a controller circuit 310 to communicate with the chemical sensor 303, a telemetry circuit 312 to communicate with the controller circuit 310 and an external module 320 (such as a programmer module), and a memory circuit 314 to communicate with the controller circuit 310. The chemical sensor 303 includes a sensing element 304, an optical excitation assembly 306, and an optical detection assembly 308. The implantable system 300 can include at least one implantable lead 322 connected to the pulse generator 302, the at least one implantable lead 322 configured to be connected to at least one implantable electrode 324 capable of electrically stimulating tissue. The implantable system 300, can include a chemical sensing lead to electrically or optically couple the pulse generator 302 with the chemical sensor 303.

Figure 4:
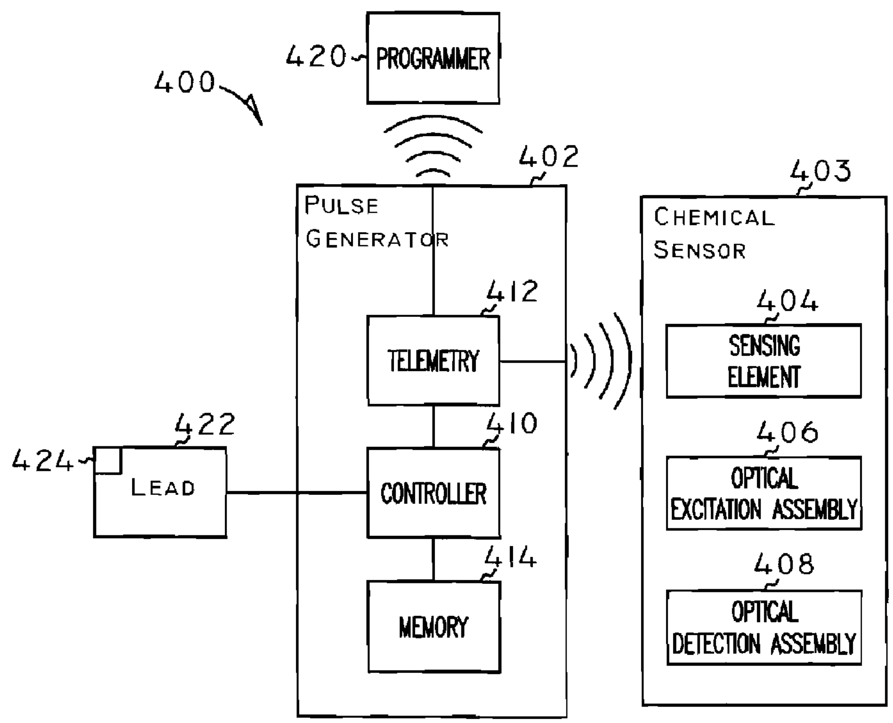
FIG. 4 schematically illustrates an IMD with a chemical sensor in accordance with another embodiment of the invention.

FIG. 4 illustrates an embodiment of an implantable system 400 having a pulse generator 402 in wireless communication with a chemical sensor 403. The pulse generator 402 can include a controller circuit 410, a telemetry circuit 412 to communicate with the controller circuit 410, the chemical sensor 403, and an external module 420 (such as a programmer module), and a memory circuit 414 to communicate with the controller circuit 410. The chemical sensor 403 includes a sensing element 404, an optical excitation assembly 406, and an optical detection assembly 408. The implantable system 400 can include at least one implantable lead 422 connected to the pulse generator 402, the at least one implantable lead 422 configured to be connected to at least one implantable electrode 424 capable of electrically stimulating tissue. In this embodiment, the pulse generator 402 is in wireless communication with the chemical sensor 403. It will be appreciated that wireless communication can be achieved through various approaches including radio frequency links, ultrasonic links, acoustic links, and the like. In some embodiments, the chemical sensor 403 can be in a self-contained device with its own internal power supply and radio frequency or acoustic communication capability (having a radio frequency communication link, an ultrasonic communication link, and/or an acoustic communication link).

Figure 5:
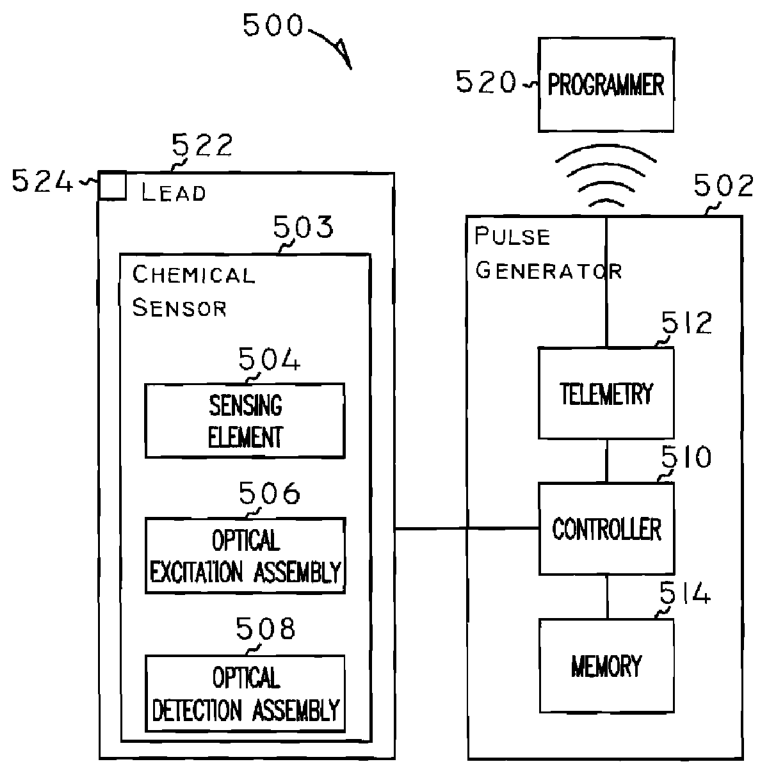
FIG. 5 schematically illustrates an IMD with a chemical sensor in accordance with another embodiment of the invention.

FIG. 5 illustrates an embodiment including a system 500 having a pulse generator 502 and a chemical sensor 503 integrated with a lead 522. The lead 522 is coupled to the pulse generator 502. The chemical sensor 503 can be coupled to the lead 522 at any point between the proximal and distal ends of the lead 522. In an embodiment, the chemical sensor 503 is coupled to the distal end of the lead 522. The chemical sensor includes at least one sensing element 504, at least one optical excitation assembly 506 and at least one optical detection assembly 508.

Figure 6:
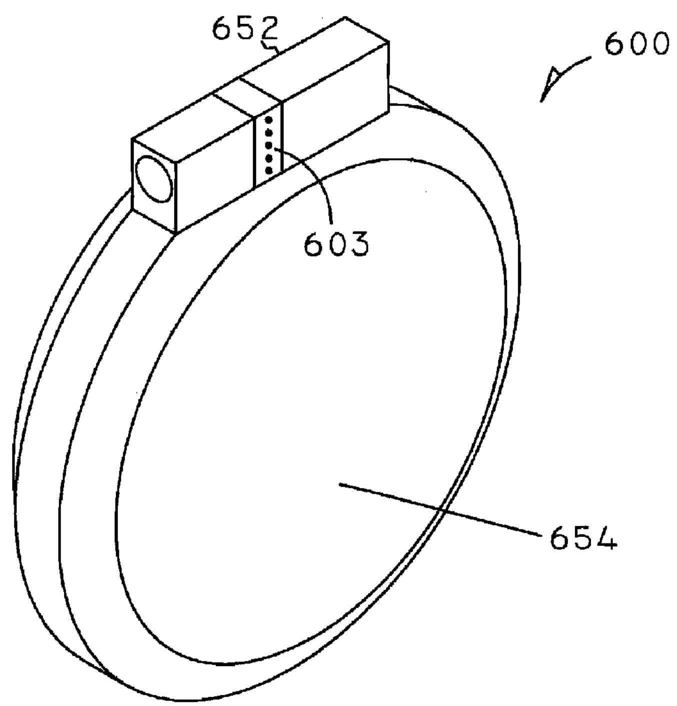
FIG. 6 illustrates an implantable medical device (IMD) with a chemical sensor in the header, according to various embodiments.
Figure 7:
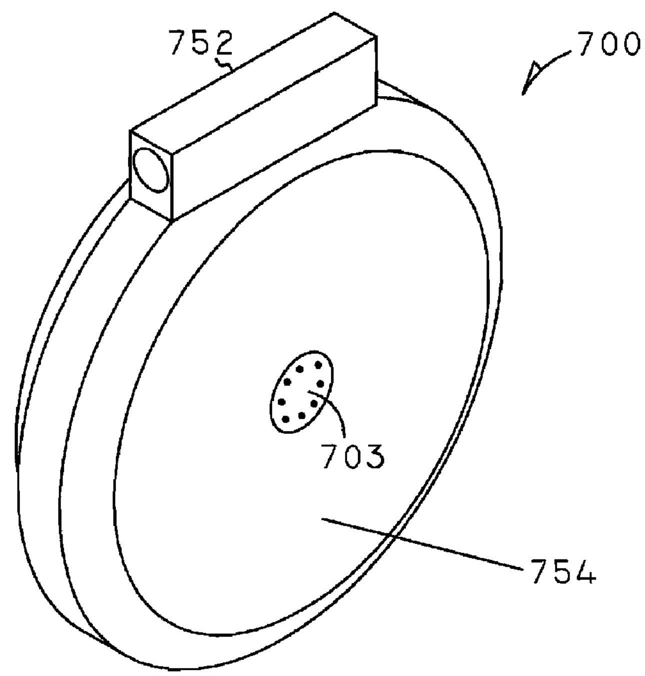
FIG. 7 illustrates an implantable medical device (IMD) with a chemical sensor integrated with the body of the device, according to various embodiments.

FIG. 6 illustrates an embodiment of an implantable medical device (IMD) 600 with an integrated chemical sensor 603 in the header 652. The IMD 600 includes a housing or body 654. In this embodiment, the chemical sensor 603 is located in the IMD device header 652 which is in turn coupled to the housing 654. FIG. 7 illustrates an embodiment of an implantable medical device (IMD) 700 with an integrated chemical sensor 703 disposed on the device housing 754. In this embodiment, the chemical sensor 703 is coupled to the device housing 754. According to various embodiments, circuitry for correction of cardiac arrhythmias uses a common battery with the excitation assembly. Circuitry for correction of cardiac arrhythmias is configured to communicate with the detection assembly directly or indirectly, according to various embodiments.

Figure 8:
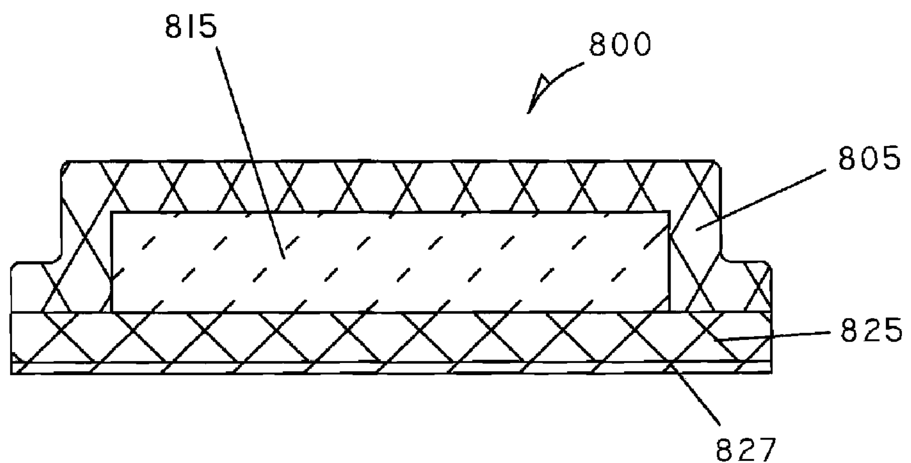
FIG. 8 is a cross-sectional view of a sensing element, according to various embodiments.

It will be appreciated that the sensing element may take on various structural configurations. Referring now to FIG. 8, a cross-sectional view of a sensing element 800 for measuring ion concentration is shown according to some embodiments. The sensing element 800 includes an optically transparent backing layer 825, an adhesive or bonding layer 827 under the backing layer 825, an indicator element 815 attached to the membrane, and an overcoat layer 805.

The indicator element 815 can include a polymeric support matrix and one or more ion selective sensors as described more fully below. Physiological analytes can diffuse through the overcoat layer 805 and into the indicator element 815 where they can bind with the ion selective sensor to produce a fluorimetric or calorimetric response.

The backing layer 825 can be configured to provide support (e.g. stiffness and handling capability) for the sensing element 800. The backing layer 825 can be transparent and essentially impermeable to, or much less permeable than the overcoat layer 805 to the solution in which a target analyte is present, such as blood, interstitial fluid, or a calibrating solution. The backing layer 825 can allow the signal or signals, such as the optical signals, from the indicator element 815, to pass there-through. Particularly useful materials of construction for this backing layer 825 include polymeric materials such as polyesters, polycarbonates, polysulfones including but not limited to polyethersulfones and polyphenylsulfones, polyvinylidine fluoride, polymethylpentenes, and the like.

The backing layer 825 can be adhesively bonded or thermally fused to the indicator element 815. In embodiments where the backing layer 825 is adhesively bonded to the indicator element 815, the bonding adhesive can be essentially transparent to light used in excitation of the sensing element 800 and to light emitted or reflected there-from. An exemplary adhesive is FLEXOBOND 431™ urethane adhesive (Bacon Co., Irvine, Calif.).

The adhesive or bonding layer 827 can serve to couple the sensing element 800 to a substrate. The adhesive or bonding layer 827 can include a bonding adhesive. The bonding adhesive can be essentially transparent to light used in excitation of the sensing element 800 and to light emitted or reflected there-from. An exemplary adhesive is FLEXOBOND 431™ urethane adhesive (Bacon Co., Irvine, Calif.).

The overcoat layer 805 can include a material that is permeable to the analyte of interest. The overcoat layer 805 can be opaque so as to optically isolate the indicator element 815 from the tissues surrounding the sensing element 800 in vivo. Alternatively, a separate opaque layer can be disposed over or under the overcoat layer 805. The overcoat layer 805 can include a polymeric material with an opacifying agent. Exemplary opacifying agents can include carbon black, or carbon-based opacifying agents, ferric oxide, metallic phthalocyanines, and the like. In a particular embodiment, the opacifying agent is carbon black. Opacifying agents can be substantially uniformly dispersed in the overcoat layer 805, or in a separate layer, in an amount effective to provide the desired degree of opacity to provide the desired optical isolation. The sensing element 800 can also include an opaque ink coating applied using a variety of techniques, such as an inkjet technique or an ink-screening technique. The sensing element 800 can also include a black membrane. For example, it can include a black DURAPORE® membrane (available from Millipore as a white membrane which is then treated with black ink).

Figure 9:
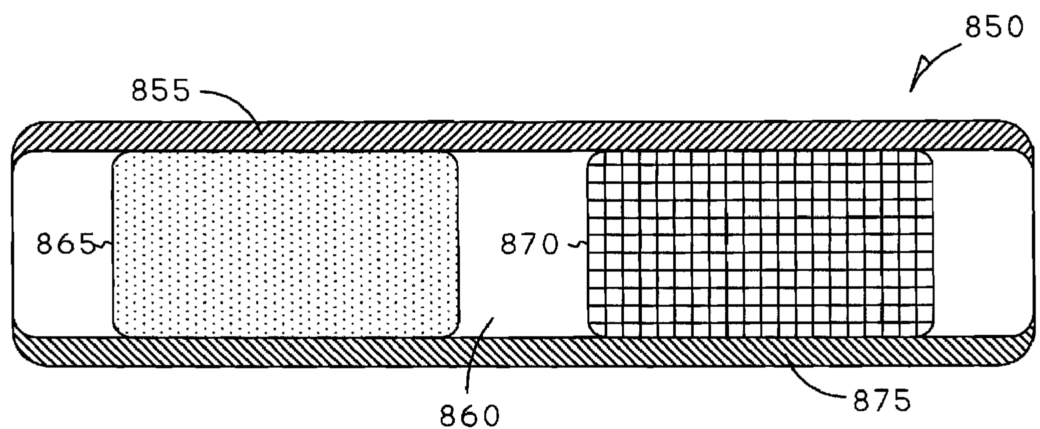
FIG. 9 is a cross-sectional view of a sensing element, according to another embodiment of the invention.

FIG. 9 illustrates a cross-sectional view of a sensing element 850 for measuring analyte concentration, according to various embodiments. The sensing element 850 includes a first indicator element 865 and second indicator element 870. In an embodiment, the first indicator element 865 can be an analyte indicating element while the second indicator element 870 can be an analyte insensitive element for optical referencing purpose, or more generally, as a negative control. In another embodiment, the first indicator element 865 is specific for one analyte while the second indicator element 870 is specific for a different analyte of interest. In another embodiment, indicator elements 865 and 870 can be accompanied by other indicator elements including analyte sensitive and insensitive elements forming an indicator array. In some embodiments, concentrations of a plurality of analytes can be sensed. For example, concentrations of between 1 and 20 analytes can be sensed in some embodiments.

In the embodiment shown in FIG. 9, analytes from a bodily fluid diffuse through a membrane 855 and reversibly bind with an ion selective sensor disposed within the indicator elements. Many different ion selective sensors or systems can be used. Exemplary ion selective sensors and systems are described in greater detail below. The indicator element can include a polymeric support. The polymeric support can include an ion permeable polymeric matrix. Specifically, the polymeric support can include a polymeric matrix permeable to sodium ions, potassium ions, and hydronium ions. The polymeric support can include a hydrophilic polymer. In an embodiment, the polymeric support can include one or more of cellulose, polyvinyl alcohol, dextran, polyurethanes, quaternized polystyrenes, sulfonated polystyrenes, polyacrylamides, polyhydroxyalkyl acrylates, polyvinyl pyrrolidones, polyamides, polyesters, and mixtures and copolymers thereof.

The membrane 855 can include an ion permeable polymeric matrix. For example, the membrane 855 can include a polymeric matrix permeable to sodium ions, potassium ions, and hydronium ions. In some embodiments, the membrane 855 includes a hydrophilic polymer. Various types of polymers can be used to form the membrane 855. By way of example, the membrane can include one or more of cellulose, polyvinyl alcohol, dextran, polyurethanes, quaternized polystyrenes, sulfonated polystyrenes, polyacrylamides, polyhydroxyalkyl acrylates, polyvinyl pyrrolidones, polyamides, polyesters, and mixtures and copolymers thereof.

In some embodiments, membrane 855 is opaque. For example, in some embodiments both an optical excitation assembly and an optical detection assembly are located on a side of the sensing element 850 opposite the membrane 855. In such an embodiment, rendering membrane 855 opaque can reduce background interference. In other embodiments, an opaque cover layer is disposed over membrane 855. In will be appreciated that there are many way of developing opacity in a membrane or layer including those described above.

The housing 860 can be configured to separate indicator elements 865 and 870. The housing 860 can include microwells or microcavities into which the indicator elements 865 and 870 fit. However, in some embodiments the indicator elements are disposed immediately adjacent to one another. The housing 860 can be constructed of various materials. In some embodiments, the housing 860 includes a polymeric matrix. In an embodiment, the housing 860 includes an ion permeable polymeric matrix. Base layer 875 is configured to be disposed between the indicator elements 865 and 870 and the optical detection assembly. In an embodiment, the base layer 875 is optically transparent over the wavelengths of interrogation and detection. Base layer 875 can be made of a variety of different materials including an optically transparent polymer, glass, crystal, etc. In some embodiments, base layer 875 is omitted such that components, such as the optical excitation assembly and/or optical detector assembly are in direct contact with indicator elements 865 and 870.

According to an embodiment, dual wavelengths of light are used for illumination of the one or more sensing elements to allow for differential measurements. For example, one center wavelength can excite the sensing element at an isobestic point on the spectral response curve and another center-wavelength can excite at a maximally sensitive wavelength. Another embodiment can excite the sensing element(s) using dual illumination wherein the two center wavelengths are chosen for maximal excitability but with complimentary amplitude responses. The analyte insensitive optical element is then used as an optical system drift correction signal and thereby enhances long-term accuracy. Other embodiments employ pH sensitive compartments to allow for cancellation of pH effects.

Figure 10:
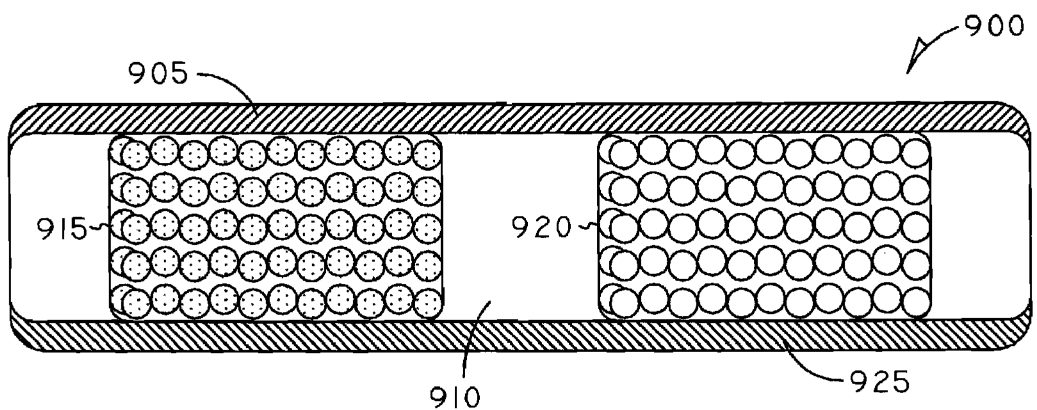
FIG. 10 is a cross-sectional view of a sensing element, according to another embodiment of the invention.

FIG. 10 illustrates a cross-sectional view of a sensing element for measuring analyte concentrations, according to various embodiments. The sensing element 900 includes a first indicator element 915 and second indicator element 920. The sensing element 900 includes a housing 910, an ion permeable membrane 905, and a base layer 925. In this embodiment, the chemistries of the sensing element 900 are integrated into or onto support beads for the purpose of increasing surface area and optical scattering effects. The sensing element 900 can be configured to be mated to the header of a pulse generator, to an optical window in the housing of a pulse generator, to a lead, or to an optical window on a sensor in wireless communications with the pulse generator (satellite sensor).

Figure 11:
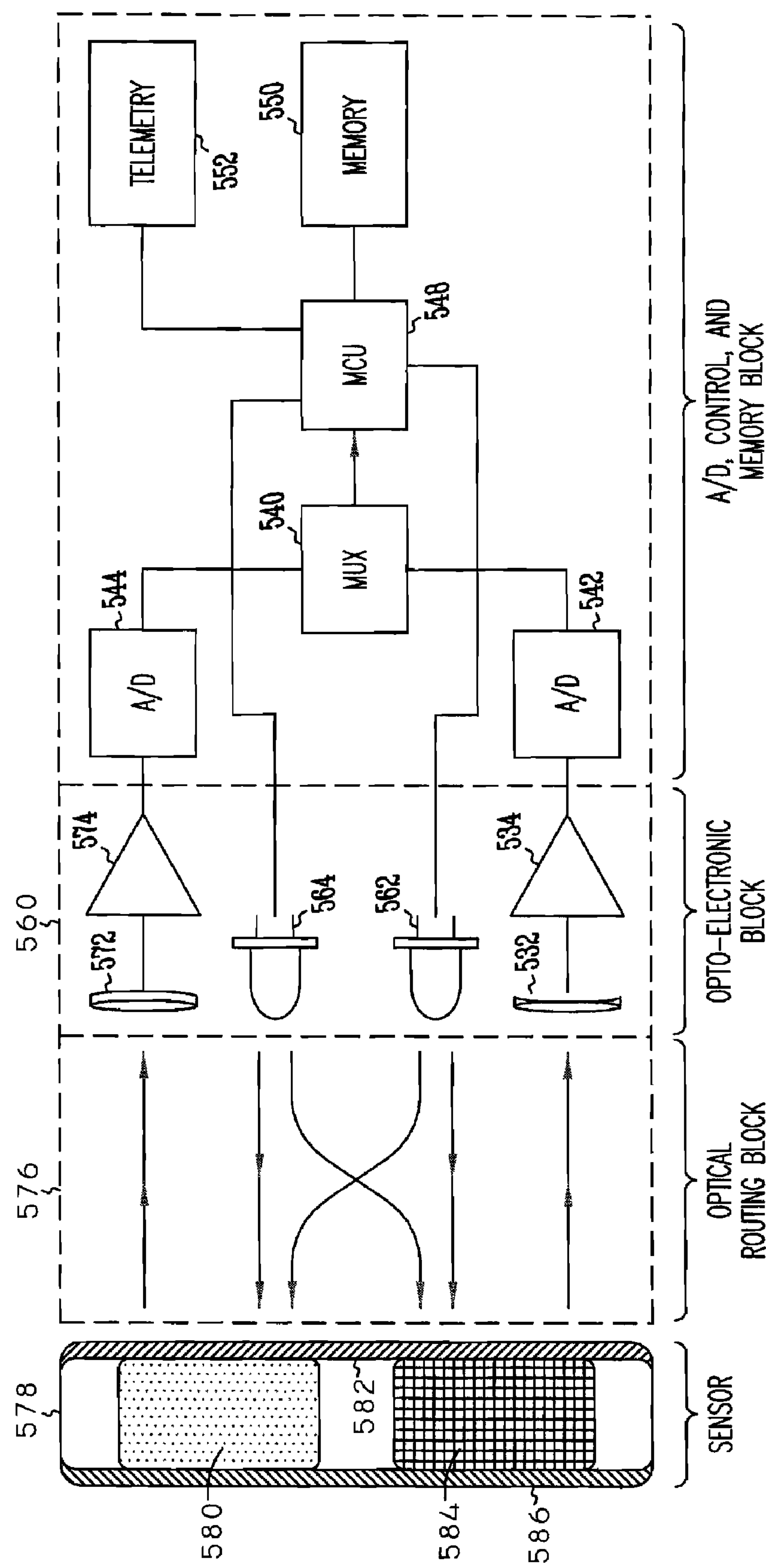
FIG. 11 schematically illustrates an embodiment of a device for measuring a physiological analyte concentration.

FIG. 11 illustrates one embodiment of a system for measuring an analyte concentration. The analyte of interest, for example potassium, is present in a bodily fluid, for example interstitial fluid, in contact with the ion permeable membrane 586 of sensing element 578. The analyte diffuses through the membrane 586 and binds with an ion selective sensor in indicator element 580. The binding of the analyte results in an absorption spectral shift and/or a change in the fluorescent intensity of the indicator element 580.

Indicator element 584 is also subject to the flux of analyte diffusing through the membrane 586. However, in this embodiment indicator element 584 is designed to be optically invariant to analyte concentrations and thus can serve as a negative control. In this embodiment, indicator element 584 can also be referred to as an optical reference element.

The diffuse reflectance spectra of indicator element 580 and optical reference element 584 are detected by first illuminating indicator element 580 and optical reference element 584 with emitters 562 and 564 (optionally in conjunction with optical filters.) Emitters 562 and 564, located within optoelectronic block 560, can be configured to produce light at two different center-wavelengths (e.g., wavelength 1 and wavelength 2 respectively) selected to effectively interrogate the spectral reflectance changes of indicator element 580 as the analyte concentration changes. Emitters 562 and 564 can be turned on and off alternately, under control of microprocessor control unit (MCU) 548 so that only one wavelength of reflectance is interrogated at a time. The light can be coupled from each of the emitters 562 and 564 to each of the indicator element 580 and the optical reference element 584 by means of an optical routing block 576. Diffusely reflected light, or emitted light in the case of a fluorescent sensor, is then routed from indicator element 580 and optical reference element 584, through optically transparent membrane 582, to sensor optical detector 572 and reference optical detector 532, respectively, by means of the optical routing block 576. The optical routing is achieved by means of optical fibers, waveguides, integrated optical packing of emitter and detector subassemblies, by free-space optics, or by other means known by those skilled in the art. The optical detectors 572 and 532 produce an electrical current that can be amplified by circuits 574 and 534 respectively to result in voltage signals indicative of the reflected light intensity returned from the indicator element 580 and the optical reference element 584 respectively. These analog voltage signals can then be processed by A/D converters 544 and 542, respectively, to produce digital signals and can then be routed through a multiplexer (MUX) 540. The resulting data is processed by MCU 548 and stored in memory 550 or routed to telemetry unit 552.

As the concentration of the analyte changes, the optical characteristics of indicator element 580 change, while the optical characteristics of the optical reference element 584 do not change. In one embodiment, MCU 548 can take the digitized emission or reflectance signal at a particular wavelength associated with excitation of the indicator element 580 and then calculates a corrected signal based upon the digitized signals associated with optical reference element 584. The MCU 548 can then take the digitized emission or reflectance signal at a second wavelength associated with excitation of the indicator element 580 and calculates a second corrected signal based upon the digitized signals associated with optical reference element 584. The MCU 548 can then use the ratio of corrected optical signals at the two wavelengths in estimating analyte concentration. This ratio is processed by MCU 548 by a program routine or lookup table into representations of analyte concentration. Resulting data can be stored, transmitted to external devices, or integrated into the functions of an accompanying therapeutic device.

Embodiments of chemical sensors of the invention may be calibrated initially and/or periodically after implantation to enhance accuracy. It will be appreciated that calibration can be performed in various ways. By way of example, after the chemical sensor is implanted, blood can be drawn and analyte concentrations in the blood can be assessed using standard in vitro laboratory techniques. The concentrations indicated by the in vitro testing can then be compared with the concentrations indicated by the implanted device, and the implanted device can then be corrected (offset correction) based on the difference, if any. The offset correction value can be stored in circuitry in the pulse generator and automatically applied to future measurements. In some embodiments, this correction procedure is performed after the foreign body response has formed a tissue pocket around the implanted device. In some embodiments, this correction procedure is performed at regular intervals.

The chemical sensor can measure the concentration of one or more analytes, such as sodium ions and potassium ions, at a programmable rate (using a programmable timer), according to an embodiment. The chemical sensor can also be configured to measure concentrations of analytes on demand, as dictated by a program routine or as initiated by an externally communicated command. The analyte concentration measurements can be equally spaced over time, or periodic, in an embodiment. For example, the optical excitation assembly can be configured to interrogate the sensing element periodically. The measurements can be taken at various times in a non-periodic manner, or intermittently, in an embodiment. In one embodiment, a measurement is made approximately once per hour.

The power consumption of an optical chemical sensor system can be significantly greater than that of an electrochemical sensor system configured for similar performance. This is particularly true in the context of an optical chemical sensor including an optical excitation assembly. Chemical sensors of the invention can be designed as part of a chronically implantable system and therefore power consumption can be a performance limiting characteristic. As such, embodiments of the invention can include methods to reduce average and peak power consumption from an energy source, such as a battery.

Figure 12:
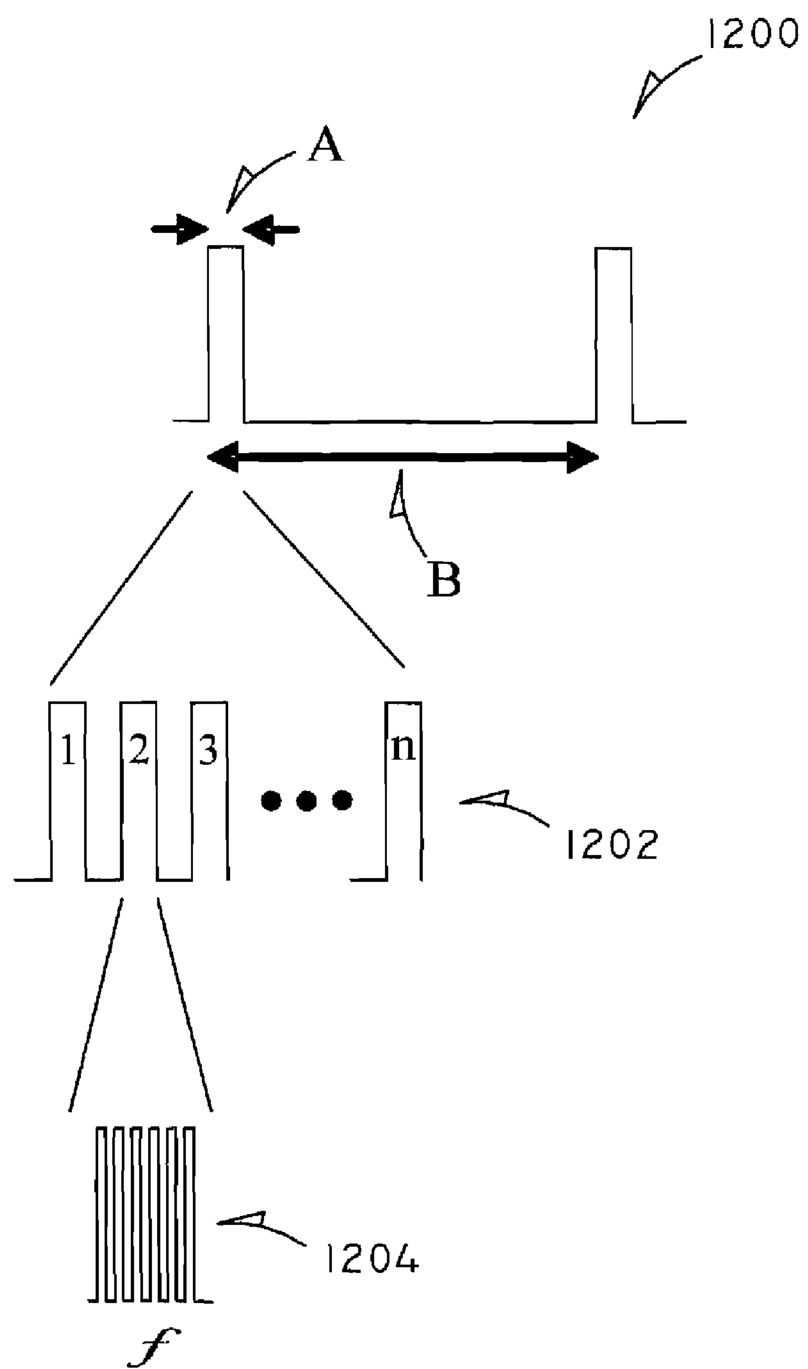
FIG. 12 schematically illustrates a duty cycling scheme for operation of an optical sensor in accordance with an embodiment of the invention.

Referring now to FIG. 12, a schematic illustration of a power management system is shown that can reduce battery load while preserving system performance. In FIG. 12, interval "A" depicts the duration of observation of the sensed parameter. Interval "B" depicts the maximum duration between observations of the sensed parameter. Interval "B" should be as long as possible for the best energy savings, but it must be short enough so that rapid changes in the observed system are tracked by the detector. It will be understood that this system can be optimized based on the temporal characteristics of the analyte of interest. For example, if the sensor is intended to measure potassium levels, the maximum rate of change for potassium concentrations in the target physiological system can be taken into account. In other words, the particular analyte being measured can directly impact factors such as the maximum duration between observations of the sensed parameter. In an embodiment, the LED can be turned on for a portion of the duration of observation. The percentage of time that the LED is turned on during the duration of observation can be referred to as the duty factor of sampling.

The ratio of A/B multiplied by the duty factor of sampling represents the fraction of energy used by the system compared to a continuous mode detection scheme. For example, assuming the duration of observation is 100 milliseconds, the maximum duration between observations is 3600 seconds (1 hour), and the duty factor is 50%, then the final energy fraction is 0.0000138. In other words, based on these assumptions, the sensor will use approximately 1/72,000th of the energy in a semi-continuous duty factor mode than in continuous mode. It will be appreciated that many different durations of observation are contemplated herein. In addition, many different maximum durations between observations are contemplated herein such as 1 minute, 10 minutes, 30 minutes, 60 minutes, 120 minutes, 180 minutes, etc.

In many embodiments, the dominant energy consuming portion of the sensor system will be the light source, if operated in a continuous mode. A typical light source can consume 2 milliAmps, an amount unacceptably high for most chronically implanted devices. However, using the described duty factoring scheme, in one example, the average current consumed can be reduced to 28 nanoAmps. It will be appreciated that the results of the duty factoring scheme will depend on various factors including the particular duration of observation, the maximum duration between observations, and the effective duty factor.

Embodiments of the invention can also include methods for reducing noise and uncertainty in the system responses including modulation/demodulation and multiple sampling events. Modulation reduces the sensor susceptibility to external light sources and to DC offsets in the received signal. By way of example, the stimulating light source can be turned on at a specific frequency 1204 "frequency f" and the receive circuit can have a filter that rejects signals outside of a narrow band that includes frequency f. In addition, the receive circuit includes a demodulator that responds preferentially to signals of frequency f. These features can reduce or eliminate any system response to signals from sources other than the intended optical source.

Multiple sampling events 1202 within the sampling interval provide lower peak current demands from the power supply during the sample event. These also provide multiple signals which can be integrated and averaged to reduce the effects of random noise sources and increase accuracy. The generation of sample intervals, sample events, and the processing of the sensor information can be performed by a microprocessor control unit/timer. The microprocessor control unit can then send the data to memory or communicate with other components of a patient management system.

Embodiments of the invention can include a sensing element including one or more ion selective sensors. Ion selective sensors may either rely on surface phenomena or on concentration changes inside the bulk of a phase. Ion selective sensors can include optical sensors, including both non-carrier optical sensors and carrier-based optical sensors, and ion-selective electrodes (ISEs).

In an embodiment, the ion selective sensor is fluorimetric. Fluorimetric ion selective sensors exhibit differential fluorescent intensity based upon the complexing of an analyte to a complexing moiety. In an embodiment, the ion selective sensor is calorimetric. Colorimetric ion selective sensors exhibit differential light absorbance based upon the complexing of an analyte to a complexing moiety.

In some embodiments, the ion selective sensor comprises a non-carrier or carrier-based fluorescent or calorimetric ionophoric composition that comprises a complexing moiety for reversibly binding an ion to be analyzed, and a fluorescing or calorimetric moiety that changes its optical properties as the complexing agent binds or releases the ion. The complexing agents of the invention can optionally be appended with one or more organic substituents chosen to confer desired properties useful in formulating the ion sensing composition. By way of example, the substituents can be selected to stabilize the complexing agent with respect to leaching into the solution to be sensed, for example, by incorporating a hydrophobic or polymeric tail or by providing a means for covalent attachment of the complexing agent to a polymer support within the ion selective sensor.

Non-Carrier Ion Sensors

In an embodiment, the ion selective sensor is a non-carrier optical ion sensor. Non-carrier optical ion sensors can include a hydrophilic indicator dye that is covalently attached to a hydrophilic polymer matrix (substrate), and which selectively complexes the ion of interest to directly produce either a calorimetric or fluorescent response. In an embodiment of a non-carrier ion selective sensing element, a fluoroionophore is covalently bonded to a suitable substrate. A fluoroionophore is a compound including both a fluorescent moiety and an ion complexing moiety. As an example, (6,7-[2.2.2]-cryptando-3-[2"-(5"-carboethoxy)thiophenyl]coumarin, a potassium ion selective fluoroionophore, can be covalently attached to an azlactone functional hydrophilic porous polyethylene membrane to produce a fluorescence-based $K^+$ non-carrier ion sensor. As another example, hydroxypyrene trisulfonate, a hydrogen ion selective fluoroionophore, can be covalently attached to an amine functional cellulose to produce a fluorescence-based pH non-carrier ion sensor. The fluoroionophore can be covalently bonded to a substrate by any useful reactive technique, which may depend upon the chemical functionality of the particular fluoroionophore. The substrate can, in turn, be attached to a backing membrane or layer.

A specific example of a non-carrier potassium ion sensor includes a sensing layer that includes 6,7-[2.2.2]-cryptando-3-[2"-(5"-carboxy)furyl]coumarin (FCCC) covalently bonded to a crosslinked amine functional cellulose membrane (CUPROPHAN™; Enka AG, Ohderstrasse, Germany), the sensing layer being adhered to a polycarbonate backing membrane by FLEXOBOND 430™ urethane adhesive and the backing membrane having coated thereon CW14™ pressure-sensitive adhesive on a release liner. Another specific example of a non-carrier potassium ion sensor includes a sensing layer that includes 6,7-[2.2.2]-cryptando-3-[2"-(5"-carboxy)furyl]coumarin covalently bonded to a crosslinked azlactone functional hydrogel with a linker such as a diamine linker. The sensing layer can then be photocrosslinked within the cavity of a substrate, such as a microwell, or the gel capsule of a satellite sensor. The term satellite sensor can be used to describe implanted chemical sensors that are remote from the pulse generator.

A specific example of a non-carrier sodium ion sensor includes a sensing layer having 6,7-[2.2.1]-cryptando-3-[2"-(5"-carboxy)furyl]coumarin covalently bonded to a crosslinked amine functional cellulose membrane (CUPROPHAN™; Enka AG, Ohderstrasse, Germany), the sensing layer being adhered to a polycarbonate backing membrane by FLEXOBOND 430™ urethane adhesive and the backing membrane having coated thereon CW14™ pressure-sensitive adhesive on a release liner.

A specific example of a non-carrier hydrogen ion sensor includes a sensing layer that includes hydroxypyrene trisulfonate covalently bonded to a crosslinked amine functional cellulose membrane (CUPROPHAN™; Enka AG, Ohderstrasse, Germany), the sensing layer being adhered to a polycarbonate backing membrane by FLEXOBOND 430™ urethane adhesive and the backing membrane having coated thereon CW14™ pressure-sensitive adhesive on a release liner.

An exemplary class of fluoroionophores are the coumarocryptands. Coumarocryptands can include lithium specific fluoroionophores, sodium specific fluoroionophores, and potassium specific fluoroionophores. For example, lithium specific fluoroionophores can include (6,7-[2.1.1]-cryptando-3-[2"-(5"-carboethoxy)furyl]coumarin. Sodium specific fluoroionophores can include (6,7-[2.2.1]-cryptando-3-[2"-(5"-carboethoxy)furyl]coumarin. Potassium specific fluoroionophores can include (6,7-[2.2.2]-cryptando-3-[2"-(5"-carboethoxy)furyl]coumarin and (6,7-[2.2.2]-cryptando-3-[2"-(5"-carboethoxy)thiophenyl] coumarin.

Suitable fluoroionophores include the coumarocryptands taught in U.S. Pat. No. 5,958,782, the disclosure of which is herein incorporated by reference. Such fluorescent ionophoric compounds can be excited with GaN blue light emitting diodes (LEDs) emitting light at or about 400 nm. These fluorescent ionophoric compounds have ion concentration dependent emission that can be detected in the wavelength range of about 450 nm to about 470 nm.

The substrate can be a polymeric material that is water-swellable and permeable to the ionic species of interest, and insoluble in the medium to be monitored. Exemplary substrate materials include, for example, ion-permeable cellulose materials, high molecular weight or crosslinked polyvinyl alcohol (PVA), dextran, crosslinked dextran, polyurethanes, quaternized polystyrenes, sulfonated polystyrenes, polyacrylamides, polyhydroxyalkyl acrylates, polyvinyl pyrrolidones, hydrophilic polyamides, polyesters, and mixtures thereof. In an embodiment, the substrate is cellulosic, especially ion-permeable crosslinked cellulose. In an embodiment, the substrate comprises a regenerated cellulose membrane (CUPROPHAN™, Eenka AG, Ohderstrasse, Germany) that is crosslinked with an epoxide, such as butanediol diglycidyl ether, further reacted with a diamine to provide amine functionality pendent from the cellulose polymer. In an alternate embodiment, the substrate comprises azlactone functional hydrophilic porous polypropylene that has been amine functionalized using a diamine functionality pendent to the azlactone.

In one approach to making a non-carrier ion selective sensor, aminoethylated cellulose is first activated by treatment with a sodium bicarbonate solution. A fluoroionophore, such as 6,7-[2.2.2]-cryptando-3-[2"-(5"-carboxyl)furyl]coumarin, is then covalently bonded to the aminoethylated cellulose. Optionally, once the desired amount of the fluoroionophore is covalently bonded to the aminoethylcellulose, remaining amino groups are blocked by acylation. Next, the fluoroionophore bearing cellulose is then taken up into solution and then coated or deposited on an optical fiber or in a microcavity of a housing.

Permeability enhancing agents can be added to the composition used to form the sensing layer to increase the ion permeability of the sensing layer. Suitable permeability enhancing agents can include small molecular weight molecules which are hydrophilic and are water soluble. Such agents can include sugars, polyols and the like. As a specific example, glycerol can be used. Another specific example includes low molecular weight water soluble polyvinylalcohol.

In some embodiments, the sensing layer materials can be prepared utilizing a photocrosslinkable hydrogel having reactive functional groups for covalently attaching chemically functionalized fluoroionophores and chromoionophores. In an embodiment, the photocrosslinkable hydrogel can include azlactone functional copolymers. The azlactone functional copolymers can be crosslinked (cured) using photocrosslinking agents such as bisazides, bisdiazocarbonyls, and bisdiazirines. This type of crosslinking does not affect the azlactone groups, but creates a three dimensional hydrogel matrix. The azlactone functional polymers can then be reacted with chromoionophores or fluoroionophores having reactive functional groups (such as primary amines, secondary amines, hydroxyl groups, and thiol groups). The reactive functional groups then react, either in the presence or absence of suitable catalysts, with the azlactones by nucleophilic addition to produce a covalent bond. The covalent bonding step can be carried out before or after coating, before or after curing, and before or after patterning.

Optionally, after ion sensing molecules are covalently attached, capping groups can be added to occupy any unused functional groups, such as azlactone groups, and prevent later contamination of the gel by any unwanted material. The capping group may hydrophilic (e.g. water) to improve the swellability of the gel. Alternatively, the capping group can be hydrophobic to provide a microenvironment compatible with carrier based ion selective sensors, as described more fully below.

The sensing layer materials can be configured in various ways depending on the particular application. In some embodiments, the sensing layer materials are configured in a substantially planar configuration. In other embodiments, the sensing layer materials are configured as beads or microdots.

Curing of sensing layer compositions can be performed using light or heat depending on the particular application and the chemical makeup of the sensing layer materials.

Carrier Based Ion Sensors

In an embodiment, the ion selective sensor is a carrier based ion sensor. Carrier based ion sensors include a compound, referred to as an ionophore, that complexes with and serves to carry the ion of interest. Carrier based ion sensors can include both optical ion sensors and ion selective electrodes. In some embodiments, carrier based optical ion sensors include a lipophilic ionophore, and a lipophilic fluorescent or calorimetric indicator dye, called a chromoionophore. The chromoionophore and the ionophore can be dispersed in, and/or covalently attached to, a hydrophobic organic polymeric matrix. The ionophore can be capable of reversibly binding ions of interest. The chromoionophore can be a proton selective dye. In operation, ions of interest are reversibly sequestered by the ionophores within the organic polymer matrix. To maintain charge neutrality within the polymer matrix, protons are then released from the chromoionophore, giving rise to a color or fluorescence change.

A specific example of a carrier based ion sensor includes potassium ionophore III, chromoionophore I, and potassium tetrakis(4-chlorophenyl)borate dispersed in a polymer matrix made from polyvinylchloride and bis(2-ethylhexyl)sebacate surfactant to produce a colorimetric $K^+$ sensing element.

The hydrophobic organic polymeric matrix can include materials with sufficient tensile strength, chemical inertness, and plasticizer compatibility. Exemplary materials can include poly(vinyl chloride), derivatives of polyvinyl chloride, polyurethane, silicone rubbers, polyalkylmethacrylates, and polystyrene.

In an embodiment, the hydrophobic organic polymer matrix is made permeable to the analyte of interest with plasticizers. Suitable plasticizers can include 2-nitrophenyl octyl ether (NPOE), dioctyl sebacate (DOS), bis(2-ethylhexyl)sebacate (BEHS), dibenzyl ether (DBE), and the like. However, it is known that plasticizers can leach out of the hydrophobic organic polymer matrix over time. This may lead to decreased functioning of the sensor. Accordingly, in some embodiments, the sensing element includes a polymeric matrix that is self-plasticizing. Such polymers can include polyurethanes, polysiloxanes, silicone rubber, polythiophenes, epoxyacrylates, and methacrylic and methacrylic-acrylic copolymers. In an embodiment, ion selective polymer materials are produced with an acrylate backbone and a plurality of pendant lipophilic plasticizing groups derived from acrylate co-monomers. The lipophilic plasticizing groups can, for example be a pendant $C_{3-7}$ alkyl group that renders the polymer matrix inherently soft (e.g. a glass transition temperature (Tg) of less than −10° C.) and does not require additional plasticizers, i.e. the polymer is in effect self-plasticizing, so that the problem of leaching of the plasticizer does not arise.

In some embodiments, a lipophilic anion (ion-exchanger) is included to improve ion selectivity by stabilizing the concentration of the ion-ionophore complex. For example, tetraphenylborate derivatives can be used as an ion-exchanger in cation-selective polymer membrane electrodes and bulk optical sensors. In addition to reducing anion interference, tetraphenylborates can also decrease membrane resistance, and improve ionophore selectivity by stabilizing the concentration of ion-ionophore complex. The delocalized monoanionic charge that these compounds possess, in combination with their sterically hindered molecular structure make them very weakly coordinating. This is a characteristic that leads to weak, non-specific ion pair formation and maximum ionophore-mediated selectivity of the membrane. Specific lipophilic anions can include potassium tetrakis(4-chlorophenyl) borate), designated KTpClPB; sodium tetrakis[3,5-bis(1,1,1,3,3,3-hexafluoro-2methoxy-2-propyl)phenyl]borate, designated NaHFPB; potassium tetrakis[3,5-bis(trifluoromethyl)phenyl]borate, designated KTFPB; sodium tetrakis(4-fluorophenyl)borate, combinations thereof, and the like. Compounds that can be suitable alternatives to tetraphenylborates include 3,5[bis-(trifluoromethyl)phenyl]borate (NaTFPB), carboranes (such as closo-dodecacarboranes), and halogenated carboranes (such as trimethylammonium undecabromocarborane (TMAUBC), undecachloroinated (UCC), hexabrominated (HBC), and undecaiodinated (UIC) carborane anions).

The chromoionophore in a carrier based ion sensor, as mentioned above, can be a pH sensitive material. Exemplary pH sensitive chromoionophore dyes include include congo red, neutral red, phenol red, methyl red, lacmoid, tetrabromophenolphthalein, α-napholphenol, and the like. The chromoionophore can be immobilized by covalent bonding to the polymer matrix. The chromoionophore can be dissolved into the polymer matrix with the aid of a plasticizer as described above.

The ionophore and/or chromoionophore can be immobilized in the polymeric matrix in various ways. For example, in one approach the ionophore is directly grafted onto an existing polymer with reactive sites. In a second approach, two different polymers are blended together, with one of them containing the graft ionophore. A third approach includes polymerizing an acrylate functional monomer, including the ionophore as a side chain, with other monomers in a one-step polymerization method. In a fourth approach, azlactone functional acrylate polymers can undergo nucleophilic addition of an amine, hydroxyl, or thiol functional ionophores to provide a covalently bonded ionophore.

Exemplary pH responsive chromoionophores can include Chromoionophore I, (9-(diethylamino)-5-(octadecanoylimino)-5H-benzo[a]phenoxazine), "ETH 5294" CAS No. 125829-24-5; Chromoionophore II, (9-diethylamino-5-[4-(16-butyl-2,14-dioxo-3,15 ioxaeicosyl)phenylimino] benzo[a]phenoxazine), "ETH 2439" CAS No. 136499-31-5; Chromoionophore III, (9-(diethylamino)-5-[(2-octyldecyl) imino]benzo[a]phenoxazine, "ETH 5350" CAS No. 149683-18-1; Chromoionophore IV, (5-octadecanoyloxy-2-(4-nitrophenylazo)phenol), "ETH 2412" CAS No. 124522-01-6; Chromoionophore V, (9-(diethylamino)-5-(2-naphthoylimino)-5H-benzo[a]phenoxazine), CAS No. 132097-01-9; Chromoionophore VI, (4',5'-dibromofluorescein octadecylester), "ETH 7075" CAS No. 138833-47-3; Chromoionophore XI, (fluorescein octadecyl ester), "ETH 7061" CAS No. 138833-46-2.

In an embodiment, the ion selective sensor is a carrier based ion-selective electrode (ISE). Carrier based ion-selective electrodes can include many of the same materials as carrier based optical ion sensors, but without the chromoionophore. In this embodiment, the ion selective hydrophobic polymer matrix containing the ionophore can be placed on top of a reference electrode such as a Ag/AgCl electrode, with an intervening hydrogel layer containing a fixed amount of a reference electrolyte (e.g. KCl for a K+ sensor). A reference electrode without the ionophore is also provided in this embodiment. ISEs produce a measurable potentiometric change upon contact with a fluid sample containing target ions. This is driven by phase boundary potentials at both interfaces, and the diffusion potential within the ion-selective polymer matrix.

Complexing Moieties

Compounds used in both non-carrier ion sensors and carrier-based ion sensors can include complexing moieties. Suitable complexing moieties can include include cryptands, crown ethers, bis-crown ethers, calixarenes, noncyclic amides, and hemispherand moieties as well as ion selective antibiotics such as monensin, valinomycin and nigericin derivatives.

Those of skill in the art can recognize which cryptand and crown ether moieties are useful in complexing particular cations, although reference can be made to, for example, Lehn and Sauvage, "[2]-Cryptates: Stability and Selectivity of Alkali and Alkaline-Earth Macrocyclic Complexes," J. Am. Chem. Soc, 97, 6700-07 (1975), for further information on this topic. Those skilled in the art can recognize which bis-crown ether, calixarene, noncyclic amides, hemispherand, and antibiotic moieties are useful in complexing particular cations, although reference can be made to, for example, Buhlmann et al., "Carrier-Based Ion-Selective Electrodes and Bulk Optodes. 2. Ionophores for Potentiometric and Optical Sensors," Chem. Rev. 98, 1593-1687 (1998), for further information on this topic.

By way of example cryptands include a structure referred to as a cryptand cage. For cryptand cages, the size of the cage is defined by the oxygen and nitrogen atoms and the size makes cryptand cages quite selective for cations with a similar diameter. For example a [2.2.2] cryptand cage is quite selective for cations such as $K^+$, $Pb^{+2}$, $Sr^{+2}$, and $Ba^{+2}$. A [2.2.1] cryptand cage is quite selective for cations such as $Na^+$ and $Ca^{+2}$. Finally, a [2.1.1] cryptand cage is quite selective for cations such as $Li^+$ and $Mg^{+2}$. The size selectivity of cryptand cages can aid in the sensitivity of chemical sensing. When these cryptand cages are incorporated into physiologic sensing systems heavier metals such as $Pb^{+2}$ and $Ba^{+2}$ are unlikely to be present in concentrations which interfere with the analysis of ions of broader physiological interest such as $Na^+$ and $K^+$.

For crown-ether moieties the size of the 15-crown-5 cage defined by the oxygen atoms make the unit suitably selective for $Na^+$; the size of the 18-crown-6 cage makes it suitably selective for $K^+$; the size of the 21-crown-7 cage makes it quite selective for $K^+$ and nonselective for $Na^+$. $Li^+$ fits well into the cavities formed by crown ethers of sizes in the range of 12-crown-4 to 15-crown-4. Crown ethers can include lithium specific crown ethers, sodium specific crown ethers, potassium specific crown ethers, and calcium specific crown ethers. For example, lithium specific crown ethers can include 6,6-dibenzyl-14-crown-4, (7-tetradecyl-2,6,9,13-tetraoxatricyclo[$12.4.4.0^{1,14}$]docosane, and ((2S,3S)-(−)-2,3-bis(diisobutylcarbamoylmethyl)-1,4,8,11-tetraoxacyclotetradecane. Sodium specific crown ethers can include (2,6,13,16,19-pentaoxopentacyclo[18.4.4. $4^{7,12}.0.^{1,20}0^{7,12}$] dotriacontane, designated 2,3:11,12-didecalino-16-crown-5 or "DD16C5"; 4'isopropyl-4'-$OCH_2CON(C_8H_{17})_2$-dibenzo-16-crown-5, designated $Na^+$-18; 4'-decanyl-4'-(4-hydroxy-5-methyl-nitrophenyl-5-oyl)-dibenzo-16-crown-5, designated $Na^+$ 43; and 15-methyl-15-stearyl-oxymethyl-1,4,7,10,13-pentaoxacyclohexadecane, designated "ODM16C5". Potassium specific crown ethers can include naphtho-(15-crown-5); (hexanolyloxymethyl) benzo-15-crown-5; (octadecanoyloxymethyl)benzo-15-crown-5; and $K^+$-35, an anionic crown ether dye derived from benzo-15-crown-5 (nomenclature of Buhlmann et al. supra). Calcium specific crown ethers can include 4,13-di-N-octadecylcarbamoyl-3-oxabutyryl-1,7,10,16,tetra-oxa-4,13-diazacyclooctadecane or 10,19-bis[(octadecylcarbamoyl)methoxy-acetyl]-1,4,7,13,16-pentaoxa-10,1,9-diazacycloheneicosane; designated "K22E1".

Complexation of bis-(crown ether) and alkali metal ions is quite specific when the size of the cation is slightly larger than the internal cavity formed by one of the crown ether rings. This can be explained by formation of intramolecular sandwich complexes. High $Na^+$ selectivity is, for example, obtained with bis(14-crown-4) and bis(12-crown-4) compounds, even though the 14-crown-4 and 12-crown-4 cavities too small for $Na^+$. In the same way, $K^+$ selectivity is obtained with bis(15-crown-5) compounds. Bis-crown ethers can include sodium specific bis crown ethers and potassium specific bis crown ethers. Sodium specific bis crown ethers can include bis[(12-crown-4)methyl]-2-dodecyl-2-methyl-malonate; bis[(12-crown-4)methyl]-2,2-dibenzyl-malonate; 1,1-bis[(12-azacrown-4)-N-methyl]dodecane. Potassium specific bis crown ethers can include bis[(benzo-15-crown-5)-4'-ylmethyl]pimelate; bis[(benzo-15-crown-5)-4'ylmethyl]-2-dodecyl-2-methylmalonate; and 2,2-bis[3,4-(15-crown-5)-2-nitrophenylcarbamoxymethyl]tetradecane, designated "BME-44".

Hemispherands can be considered to be crown ether compounds with an extra bridge that enhances ligand preorganization. An example of sodium specific hemispherand can include the compound sold under the trade name HEMISODIUM ($Na^+$-40, nomenclature of Buhlmann et al. supra). Potassium specific hemispherands can include $K^+$-26 (nomenclature of Buhlmann et al. supra) and $K^+$-27 (nomenclature of Buhlmann et al. supra).

Non-cyclic amides can include both sodium specific non-cyclic amides and calcium specific non-cyclic amide. Sodium specific non-cyclic amides can include N,N',N"-triheptyl-N,N',N"-trimethyl-4,4',4"-propylidynetris(3-oxabutyramide), designated "ETH 227"; N,N'-dibenzyl-N,N'-diphenyl-1,2-phenylene-dioxydiacetamide, designated "ETH 157"; N,N, N',N'-tetracyclohexyl-1,2-phenylenedioxy-diacetamide, designated "ETH 2120"; and 4-octadecanoyloxymethyl-N, N,N',N'-tetracyclohexyl-1,2-phenylenedioxy-diacetamide, designated "ETH 4120". Calcium specific non-cyclic amides can include (−)-(R,R)—N,N'-bis-[11-(ethoxycarbonyl)undecyl]-N,N'-4,5-tetramethyl-3,6-dioxaoctane-diamide, designated "ETH 1001"; N,N,N',N'-tetracyclohexyl-3-oxapentanediamide, "designated ETH 129"; N,N-dicyclohexyl-N', N'-dioctadecyl-3-oxapentanediamide, "designated ETH5234".

Calixarenes can include sodium specific calixarenes and potassium specific calixarenes. Sodium specific calix[4]arenes can include 25,26,27,28-tetrakis(ethoxycarbonylmethoxy), 3,9,15,21-tert-butylcalix[4]arene; $Na^+$-20 (nomenclature of Buhlmann et al. supra); $Na^+$-42 (nomenclature of Buhlmann et al. supra); $Na^+$-33 (nomenclature of Buhlmann et al. supra); and $Na^+$-34 (nomenclature of Buhlmann et al. supra). Potassium specific calix[6]arenes and calix[4]arenecrown-5 ionophores can include 37,38,39,40,41,42-hexakis(ethoxycarbonylmethoxy)calix[6]arene; $K^+$-32 (nomenclature of Buhlmann et al. supra); $K^+$-33 (nomenclature of Buhlmann et al. supra); and $K^+$-34 (nomenclature of Buhlmann et al. supra).

Coating and Patterning of Sensors

Sensing layer compositions, in the context of both carrier and non-carrier ion sensors, can be coated with or without addition of a solvent. In some embodiments, the sensing layer components are formulated as a liquid composition to facilitate coating of the sensing layer components onto substrates using coating techniques such as spray coating or dip coating. For example, in certain embodiments, it can be advantageous to incorporate the sensing layer on the tip of a fiber optic lead or inside a capsule associated with a satellite sensor in wireless communication with a pulse generator. In these cases, it can be advantageous to spray coat or dip coat the sensing layer components onto the fiber optic lead or inside the capsule. Suitable coating methods can also include spin coating, knife coating, or roller coating.

The composition can be selectively coated to provide a patterned surface. For example, techniques including ink jet printing, offset, flexographic printing, etc. can be used to selectively coat the composition. The composition may also be knife coated onto a microstructured surface (e.g. a surface having micron scale depressions or channels) in such a way that the composition resides in microstructures, providing a patterned array of the composition. In some embodiments, the composition can be deposited into microwells or microcavities in a substrate using precision dispensing techniques, such as pin-based precision dispensing.

Beyond selective coating, patterning can also be achieved by techniques such as selective curing of the composition or selective removal of the composition from a substrate. Selective curing techniques can include selective exposure to UV light or heat. Selective UV exposure methods include exposure through a mask or photographic negative or exposure by a directed beam of light, such as a laser. After curing, remaining uncured composition can be removed, e.g. by washing, to result in a patterned coating.

In some embodiments, the composition can be patterned onto a substrate by a laser addressable thermal transfer imaging processes. In this process, a thermal transfer donor element is constructed comprising a support layer, a light-to-heat conversion layer, and a transfer layer comprising the composition to be patterned. When the donor element is brought in contact with a receptor and image wise irradiated, a melt stick transfer process occurs and the composition containing transfer layer is imaged onto the receptor. As an example, the photocrosslinkable azlactone composition described earlier can be used in the transfer layer of such a system. This photocrosslinkable azlactone composition can be reacted with chromoionophores or fluoroionophores before incorporation into the transfer layer, after incorporation into the transfer layer, or after laser addressed thermal transfer to the receptor. The azlactone composition can be thermally or photochemically crosslinked before or after the transfer process. This process offers the opportunity to prepattern different indictor elements onto a transfer layer comprising the azlactone composition prior to laser addressed thermal imaging of individual azlactone-indicator conjugates to the receptor substrate. Registration of the donor and receptor elements can be robotically altered between any or all of the transfer steps to build up desired array spacings and sizes for transferred elements on the receptor that is different from the patterning of the indicators on the transfer layer.

Methods of Operation

An embodiment of the invention includes a method for using an implantable medical device including a pulse generator to monitor concentrations of physiological analytes. The method includes sensing analyte concentrations with a chemical sensor. Sensing analyte concentrations with a chemical sensor can include exposing a sensing element to a bodily fluid. Sensing analyte concentrations with a chemical sensor can also include illuminating a sensing element with an optical excitation assembly to produce an optical return signal. Sensing analyte concentrations with a chemical sensor can further include receiving light reflected from or emitted from the sensing element using an optical detection assembly.

Methods of the invention can include periodically interrogating a sensing element to determine analyte concentrations. Methods can also include storing a digitized representation of measured analyte concentrations in a memory within the implantable medical device. In some embodiments, once the information is stored, it can be evaluated as a function of time to identify metabolic trends and events. Some embodiments also include conveying data regarding analyte concentrations and/or calculated risk indexes to another device. For example, one or more messages can be wirelessly communicated to a remote patient monitoring device, including information on the stored measured analyte concentrations. In some embodiments, the method includes reading analyte concentration periodically using a home monitoring system, such as an advanced patient management system (APM). A further embodiment includes providing trending data to show the trend of analyte concentration over time.

According to various method embodiments, a processor within the implantable medical device can be used to calculate analyte concentrations based on digitized optical signals collected from an optical sensing element and a corresponding analyte insensitive optical reference element. The method can include first correcting analyte dependent intensity readings from a sensing element at a given center-wavelength for optical offsets as measured using intensity readings from an optical reference element at that center-wavelength. The method can also include using the corrected optical signal, in conjunction with a lookup table to obtain the analyte concentration. In an embodiment, the method includes adjusting the data based on calibration coefficients stored in the memory. In various embodiments, adjustments are made based on temperature, as measured by a temperature sensor integrated into the implantable medical device. The method can also include calculating compensated analyte concentrations, taking into account various adjustments, and then storing them in memory along with an associated time stamp.

Methods of Use

In some current heart failure monitoring regimens, heart failure patients take note of weight gain, blood pressure, and other symptoms, and then self-report these symptoms via telephone to a nurse or physician who treats their condition. If their reported symptoms indicate an adverse condition that requires diuretic therapy, the caregiver has to choose between prescribing treatment over the phone, or bringing the patient to the clinic. Diuretic therapy can include the administration of diuretics as well as the administration of agents such as ACE inhibitors, beta blockers, ionotropic agents, in various combinations.

A common recommendation, often given without a blood test to measure concentrations of physiological analytes, is to administer an increased dose of diuretics and a dose of potassium. The logic of administering the dose of potassium is that it is used to offset increased losses of physiological potassium due to the increased dose of diuretics. Because actual physiological potassium concentrations are unknown in this scenario, there is a risk that the patient will end up with a potassium concentration that is too high or too low as a result. Specifically, if the patient already had high potassium levels, unknown to the caregiver, and if potassium ingestion and excretion are not properly balanced, then it is possible to suffer from hyperkalemia (potassium concentration too high). The consequences of hyperkalemia, as previously described, can include cardiac arrhythmias that sometimes result in death.

In an embodiment, the invention includes a method of monitoring diuretic therapy (such as diuretic therapy administered to a patient) using an implanted medical device. The method can include optically monitoring potassium ion concentration in a bodily fluid of a patient using an implanted medical device. The method can include determining whether the patient is suffering from hypokalemia or hyperkalemia. In an embodiment, the patient is a heart failure patient. The method includes monitoring potassium concentrations with a chemical sensor. Monitoring potassium concentrations with a chemical sensor can include exposing a sensing element to a bodily fluid. Monitoring potassium concentrations with a chemical sensor can also include illuminating a sensing element with an optical excitation assembly to produce an optical return signal. Monitoring potassium concentrations with a chemical sensor can further include receiving light reflected from or emitted from the sensing element using an optical detection assembly. Some embodiments of the method also include conveying data regarding potassium concentrations and/or calculated risk indexes to a non-implant device via a telemetry link and/or to a health professional. For example, one or more messages can be wirelessly communicated to a remote patient monitoring device.

Methods of monitoring diuretic therapy using an implanted medical device according to the invention can provide various benefits. One benefit is that a caregiver can more safely recommend a therapeutic dose of a diuretic and potassium while reducing the risk of hyperkalemia and hypokalemia. The method can allow the correct balance of diuretic and potassium to be prescribed without drawing blood from the patient. The information gathered by the implanted device can be coupled through a telemetry/remote patient management system, allowing the patient to get the optimal prescription without entering the physician's office.

In addition, the risk posed to a patient by administering increased doses of diuretics along with doses of potassium can be compounded by the patient's overall renal function. For patients with impaired renal function, the risk of becoming hyperkalemic from a dose of potassium is much greater. Even a slight potassium dose imbalance, that would be completely safe for a patient with normal kidney function, could have catastrophic destabilizing effects on a patient with impaired renal function. Therefore, methods of monitoring diuretic therapy using an implanted medical device according to some embodiments of the invention can also include optically monitoring a concentration of an analyte indicative of renal function with the implanted medical device. Specific analytes indicative of renal function can include creatinine, urea, and uric acid.

While an example of a method of monitoring diuretic therapy has been described, it will be appreciated that embodiments of the present invention can also include monitoring of other types of therapy. By way of example, embodiments of the invention can include a method for titrating drug therapy. In particular, an embodiment can include a method for controlling delivery of an active agent into a human body. The method can include measuring a physiological concentration of one or more analytes with an implanted system and varying delivery of the substance at least in part as a function of the measured concentration of the one or more analytes. The implanted system can include a pulse generator and a chemical sensor. The chemical sensor can include a sensing element, an excitation assembly, and a detection assembly. The one or more analytes can include potassium, sodium, chloride, calcium, magnesium, lithium or hydronium. The one or more analytes can include an analyte indicative of renal function. The one or more analytes can include an analyte indicative of cardiac function. In an embodiment, the active agent can comprise a diuretic. The physiological concentration of the one or more analytes can be assessed by measuring the concentration in a bodily fluid selected from the group including of blood, interstitial fluid, serum, lymph, and serous fluid.

Methods of the invention can also include providing cardiac arrhythmia therapy to a patent. By way of example, methods of the invention can include optically sensing a physiological concentration of an ion in a bodily fluid of a patient with an implanted chemical sensor. The method can further include communicating data regarding the physiological concentration of an ion to an implanted pulse generator. The method can also include altering the delivery of pulses from the implanted pulse generator to the patient based in part on the physiological concentration of an ion. Data regarding the physiological concentration of the ion can then be reported to a non-implanted device via a telemetry link. Data regarding the physiological concentration of the ion can be combined with data regarding the patient's cardio-respiratory system to form a composite profile of the patient's cardiac condition. Data regarding the patient's cardio-respiratory system can include an EKG signal, respiration rate, accelerometer data, trans-thoracic impedance, lead impedance, cardiac volume, blood pressure, weight, and cardiac necrosis signals.

Methods of providing cardiac arrhythmia therapy can also include optically monitoring a physiological concentration of an ion in a bodily fluid of the patient with an implanted chemical sensor, transmitting data regarding the physiological concentration of the ion to an implanted cardiac rhythm device, and delivering pulses from the implanted cardiac rhythm device to the patient based in part of the physiological concentration of the ion.

Methods of Optimized Diagnostic Indication

It will be appreciated that the integration of an implanted chemical sensor with the functionality of an implanted cardiac rhythm management (CRM) device enables combinations of data to be synthesized into diagnostic indicators with previously unrealized utility. As a specific example, the implanted chemical sensor can provide data regarding analyte concentrations while the CRM device functionality can provide cardiac data such as an EKG signal. As described above, the two types of data offer mutually orthogonal but linked views of the physiologic state of the patient. These two types of data, or in some embodiments more than two types, can be combined to form a composite profile of a patient's condition or composite risk index.

The value of combining the chemical sensor data with the CRM device data can be illustrated in multiple examples. One example is a method involving coordination of an electrolyte concentration signal with that of an EKG signal. A rapid or erratic heart rate is easily identified by the CRM device functionality. This data is coupled with the information from the chemical sensor, such as potassium ion concentration. As described above, an erratic heart-rate in the presence of very high or very low potassium concentrations indicates a greater level of risk to the patient than either condition separately. Methods of the invention can include embodying this logic as an algorithm and creating a warning indicator that can provide a local alert through an integrated transducer, a proximal alert from a bedside or external device in communication with the system, or a medical alert provided to a central monitoring system.

Another example is a method involving coordination of an electrolyte concentration signal with that of a respiration rate signal. CRM device functionality can include observing and identifying high respiration rates. Clinically, respiration rates can be associated with the physiological concentration of sodium ions and can indicate fluid volume overload conditions for the patient. Further, CRM device functionality can include data from an accelerometer that can verify that exercise is not the respiration driver. The combination of a volume overload signal with a verified high resting respiration rate is indicative of an imminent cardio-respiratory system crisis. Methods of the invention can include embodying this logic as an algorithm and creating a warning indicator that can provide a local alert through an integrated transducer, a proximal alert from a bedside or external device in communication with the system, or a medical alert provided to a central monitoring system.

Yet another example is a method involving coordination of EKG signal vector values with concentrations of analytes indicating cardiac tissue necrosis. Specifically, CRM device functionality can include identifying the vector component values of the EKG waveform and then categorizing these into normal or abnormal vector pattern bins. The chemical sensor can be configured to identify concentrations of troponin, cardiac specific troponin, or any other analyte that indicates cardiomyocyte necrosis. The method can include combination of the EKG vector analysis and the cardiac necrosis analyte concentration signal as part of a formalized algorithm. This method can provide greater specificity for identifying a cardiac infarct than a method based on analyzing either signal in isolation. Methods of the invention can include embodying this logic as an algorithm and creating a warning indicator that can provide a local alert through an integrated transducer, a proximal alert from a bedside or external device in communication with the system, or a medical alert provided to a central monitoring system.

While several examples of specific methods of combining data from an implanted chemical sensor with data provided by CRM device functionality have been provided, it will be appreciated that many other methods are possible based on combining data in a similar fashion. By way of example, other methods can include combining one or more of chemical sensor signals with the EKG, trans-thoracic impedance, accelerometer indicated activity, accelerometer indicated posture, heart sounds, lead impedance, cardiac volume, and other signals obtained from the CRM device. In a particular embodiment, potassium ion concentration is combined with blood pressure data.

Methods of Providing Automated Feedback

Methods described herein can be adapted to provide automatic feedback (such as indications or recommendations) to a patient regarding behavioral or pharmaceutical interventions appropriate to the stabilization, improvement, or maintenance of health. By way of example, methods can include the detection of an excessive or inadequate potassium level which can be fed into an algorithm resulting in the delivery of a message to the patient regarding the condition without caregiver intervention. The algorithm can be constructed to provide patients with recommendations for dietary and/or activity modification within a range of analyte values wherein the medical risk remains modest or negligible. The method can allow patients to reverse physiological trends before they become more serious or require the intervention of medical professionals.

In some embodiments, the method can include providing recommendations to the patient so that the patient can modulate the dose of a therapeutic agent to a more appropriate level. The method can also include providing a medical professional with data so that the medical professional can modulate the dose of a therapeutic agent and/or change the therapeutic agent.

The method can include categorizing a patient's current condition as within the bounds of self-management or requiring the intervention of a medical professional. The boundaries of these categories can be predetermined, determined adaptively by monitoring the patient norms, or set by a medical professional as desired to yield the optimal patient benefit.

The methods illustrated in this disclosure are not intended to be exclusive of other methods within the scope of the present subject matter. Those of ordinary skill in the art will understand, upon reading and comprehending this disclosure, other methods within the scope of the present subject matter.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

Aspects of the present invention may be better understood with reference to the following examples. These examples are not intended as limiting the scope of the invention.

EXAMPLES

Example 1

Determination of Ion Concentration within Pocket

The objective of this study was to evaluate the potential effects of the fibrous capsule surrounding an Implantable Cardiac Defibrillator (ICD) on sodium, potassium and glucose concentrations immediately surrounding the device. Twelve canines were implanted with an ICD device and cared for in accordance with standard laboratory procedures. After a period of time (specified in Table 1 below), fluid was collected from inside the implant encapsulation tissue (or pocket) and compared with corresponding blood serum. An amount of fluid sufficient for testing was drawn from eight of the twelve canines (insufficient amounts of fluid were collected from the other four). $K^+$, $Na^+$, Glucose, and pH and concentrations were measured using a Radiometer ABL 825 blood analyte monitor for samples from those eight canines. Serum samples were also drawn from the twelve animals and similarly analyzed with the Radiometer ABL 800 blood analyte monitor. The data is shown in Table 1 below and summarized in Table 2 below:

TABLE 1

| Relative Concentrations | | | | | |
|---|---|---|---|---|---|
| ID | Pocket Age (Days) | $K^+$ (%) | $Na^+$ (%) | Glu (%) | pH(T)c (%) |
| 1 | 61 | 128.6 | 96.8 | 7.4 | 98.7 |
| 2 | 61 | 153.8 | 99.3 | 2.5 | 102.0 |
| 3 | 57 | 119.4 | 100.7 | 0.86 | 97.6 |
| 4 | 61 | 123.7 | 98.7 | 1.18 | 100.3 |
| 5 | 64 | 148.6 | 99.3 | 3.5 | 101.6 |
| 6 | 64 | 104.9 | 102.1 | 2.3 | 92.9 |
| 7** | 74 | 127.0 | 98.6 | 29.8 | 98.0 |
| 8 | 55 | 114.3 | 100.7 | 1.05 | 97.7 |
| Range | 55-74 | 104.9-153.8 | 96.8-102.1 | 0.86-29.8 | 92.9-106.3 |

* Pocket level compared to serum level, expressed in %. <100% indicates that the level was lower in the pocket. >100% indicates that the level was higher in the pocket.
**Lead re-positioned at distal end one week after implant

TABLE 2

| Concentration Ranges | | | | |
|---|---|---|---|---|
| Range: | $K^+$ (mmol/L) | $Na^+$ (mmol/L) | Glucose (mg/dL) | pH(T)c |
| Normal* | 3.4-5.6 | 141-159 | 74-145 | 7.310-7.420 |
| Blood Serum (n = 12) | 3.5-4.2 | 146-154 | 67-119 | 7.334-7.440 |
| Pocket Fluid (n = 8) | 4.0-6.0 | 144-150 | 1-31 | 6.859-7.846 |

*Normal ranges provided by Marshfield Labs, Marshfield, Wisconsin

The data show that relative to the reference range, $K^+$ levels were normal in the blood serum and normal to slightly elevated (average ratio of 127%±16%) in the pocket fluid. The $Na^+$ levels were normal in the blood serum and the pocket fluid (average ratio 100%±2%). The glucose levels were normal in the blood serum and highly suppressed in the pocket fluid (average ratio 6%±10%). The pH levels were normal in the blood serum and varied below, within, and above the normal range in the pocket fluid. This example shows that physiological ions such as $K^+$ and $Na^+$ can be accurately measured from within an encapsulation pocket.

Example 2

Planar Ion Selective Optical Sensing Element

CUPROPHAN® cellulose sheets infiltrated with glycerol (Akzo Nobel Chemicals; Chicago, Ill.) are washed with deionized water (10 minutes) to remove the glycerol. Each sheet is stretched on a glass plate and dried at room temperature.

A. Overcoat

An overcoat solution is prepared by dissolving 4 g dextran (MW 2,000,000) in 200 mL deionized water at 50° C. Then, 2 g MARASPERSE DBOS-4® dispersing agent (Diashowa Chemicals, Inc.; Rothschild, Wis.) is added and the mixture is shaken. Thereafter, 4 g MONARCH-700® carbon black (Cabot Corp.; Waltham, Mass.) is added with sonication to produce a uniform aqueous dispersion of carbon-black. To the dispersion is added 4 g 50% (aq.) NaOH solution with mixing. Subsequently, 6 g of a 50% ethylene glycol diglycidylether (EGDGE) solution in deionized water is mixed in. The resulting overcoat solution is sprayed evenly onto the CUPROPHAN® membrane and allowed to dry.

B. Crosslinking

A solution of 3 g of 50% NaOH solution and 85 g DMSO in 350 mL deionized water is prepared. 450 g of a 50% aqueous EGDGE solution is added and mixed. This crosslinking solution is poured onto the CUPROPHAN® sheets and retained for 1 hr followed by rinsing with deionized water.

C. HDA (1,6-Hexandediamine) Reaction

Crosslinked CUPROPHAN® membranes are immersed in a solution of 120 g 70% HDA in 2.0 L deionized water for 2 hrs, rinsed with deionized water to wash off excess HDA.

D. FCCC Coupling Reaction

A dye solution is prepared by dissolving 30 mg FCCC in 30 mL DMF. Subsequently, 0.8 mL of 1,3-diisopropylcarbodiimide (DIC) and 190 mg benzotriazole hydrate (HOBt) are added and stirred for 15 minutes, after which 0.4 mL N,N-diisopropylamine (DIEA) is added with stirring. HDA-functionalized CUPROPHAN® sheets are removed from the deionized water, towel dried and immersed in the dye bath for 24 hours, after which the pieces are removed and washed with DMF, then dilute aqueous HCL (pH 2-3.5).

E. Sensor-Pulse Generator Assembly

A dye-coupled CUPROPHAN® sheet is laminated to a thin (0.175 mm) polycarbonate sheet (Bayer AG; Leverkusen, Germany) using a 2-part polyurethane adhesive such as FLEXOBOND® 430 (Bacon Industries, Inc.; Irvine, Calif.). On the polycarbonate side, a CW14™ pressure sensitive adhesive sheet (RSW Inc., Specialty Tape Div.; Racine, Wis.) is attached and the release-liner is removed. Discs are punched from the laminate using a hole-puncher and placed on an optical window of a pulse generator, configured with optoelectronics as described below for measuring potassium dependent emissions from the sensing element.

F. Optical Response of Potassium Sensor

GaN LEDs from Nichia Chemical Industries, Tokushima, Japan, or Toyoda Gosei Co., Ltd (under the brand name LEDTRONICS™) are disposed within the pulse generator and configured to be amplitude modulated at a 30 kHz carrier frequency, with a burst duration of 0.2 seconds, a repetition rate of 5 seconds, and an average output power of 2.5 mW. The light is focused, passed through a bandpass excitation filter (e.g. 390 nm±0.25 nm; % T=52%; out-of-band blocking=0.001% T; available from SpectroFilm; Woburn, Mass.), and transmitted to the sensing element through the optical window in the pulse generator. The modulated fluorescent return is similarly collected and passed through a bandpass emission filter (e.g. 475±0.35 nm; % T=64%; out-of-band blocking=0.001% T such as is available from SpectroFilm). The filtered optical signal is then be focused onto the active region of an S1337-33-BR™ photodiode detector (available from Hamamatsu Corp.; Bridgewater, N.J.) housed within the pulse generator. A small fraction of the excitation light is directly routed to the detector assembly and attenuated with a neutral density filter to provide a reference optical signal from the LED. In addition, an electronic switch is used to alternately sample the detector photo current and a 30 kHz electrical reference signal from the frequency generator. The detector output is directed to an electronic circuit within the pulse generator or satellite sensor that converts the photocurrent from the photodiode detector to a voltage. A transimpedance preamplification stage converts a photocurrent or the reference electrical signal to a voltage using an operational amplifier circuit. The following stage is a two-stage Delyiannis-Friend style bandpass filter designed to band limit the noise power while further amplifying the signal. The amplified photosignal or reference electrical signal is then digitally sampled at 100 kHz and processed to obtain a fluorescence intensity that is indicative of analyte concentration. Optionally, a pH sensor signal is also sampled and used to correct for minor pH dependent variations in the potassium sensor signal.

Example 3

Ion Selective Sensing Element in Hydrogel

A. Preparation of 1:1 Dimethylacrylamide:Vinyl Dimethylazlactone (DMA:VDM) Copolymer A solution of 70 parts dimethylacrylamide (DMA) and 70 parts 2-vinyl-4,4-dimethyl-2-oxazoline-5-one (vinyldimethylazlactone, VDM, commercially available from SNPE, Princeton, N.J.) in 210 parts methylethyl ketone (MEK) is mixed with 0.7 parts N,N'-azobis(isobutyronitrile) initiator (AIBN, commercially available as VAZO® 64, Wako Chemicals USA, Inc., Richmond, Va.). The mixture is sparged with nitrogen for 5 minutes, then sealed in ajar and tumbled in at 60® C for 24 hours.

B. Lithographic Patterning of DMA:VDM Using 4-(p-Azidosalicyamido) Butylamine (ASBA)

Under low-lighting conditions, 25 mg of 4-(p-azidosalicyamido)butylamine (ASBA, commercially available from Pierce Chemical Co., Rockford, Ill.) and 10 mg of 1-ethyl-3-(3-dimethylaminopropyl)carbodiimide promoter (EDC, HCl salt, Pierce Chemical Co., Rockford, Ill.) is dissolved in 0.5 ml of 95:5 (v/v) isopropanol:water. This solution and one drop of aq. 1N HCl are added to 1 mL of a 40% (w/w) solution of 50:50 DMA:VDM copolymer (Example 1) in MEK. Thermal coupling of the butylamine portion of ASBA to azlactone functional groups is allowed to take place for 2 hour at room temperature. The MEK solution of the resulting mixture is spin-coated onto a PMMA substrate and dried in a vacuum desiccator for 15 minutes. The sample is lithographically exposed to UV irradiation at 10-30 mW/cm$^2$ measured at 365 nm through a photomask for 3 minutes to photocrosslink through the azido portion of bound ASBA. The mask is removed and the sample is washed thoroughly with pure isopropyl alcohol, leaving gel patterns that match those of the photomask. This dual cure approach increases the efficiency for crosslinking compared to a bisazide crosslinker.

C: Preparation of Amine-Functional FCCC

The half-protected mono-N-tert-butyloxycarbonyl (t-BOC)-propylenediamine (Molecular Probes-Invitrogen) is useful for converting organic solvent-soluble carboxylic acids into aliphatic amines. Following coupling of the half-protected aliphatic diamine to the activated carboxylic acid of FCCC under standard conditions, the t-BOC group is quantitatively removed with trifluoroacetic acid. The resultant aliphatic amine derivative of FCCC is then reacted directly with azlactone functional polymer or hydrogel.

D: Preparation of FCCC Functional Hydrogel

To demonstrate the reactivity of the photo-crosslinked composition, a second sample of azlactone hydrogel is prepared and treated as follows: 50 nM of amine-functionalized FCCC is dissolved in 20 uL of carbonate bicarbonate buffer (0.05 M, pH 9.2). The indicator solution is spotted onto the photo-cured DMA:VDM coating using a needle. The sample is put in a sealed, humidified container for 2 hours at room temperature before washing with DI water and incubating in DI water for 10 hours.

Example 4

Ion-Selective Optical Sensing Element in an Ion Permeable HEMA:PEGMA Hydrogel Film A: Preparation of Acrylamide Functional FCCC Amine-functional FCCC, prepared as described in Example 3 is reacted with the succinimidyl ester of 6-((acryloyl)amino)hexanoic acid (Molecular Probes-Invitrogen) under standard conditions to yield acrylamide functional FCCC.

B: Fabrication of Polyhema Layer

A solution of 40 wt. % hydroxyethyl methacrylate (HEMA), 8.3 wt. % poly(ethyleneglycol)methacrylate (PEGMA, Mn ca 360), 1.5 wt. % acrylamide functional FCCC, 50% deionized water and 0.2 wt. % Irgacure 651 is put into a mold consisting of two slide glasses, one having a hydrophobic octadecasilane treated surface, the other having a trimethyoxysilylpropylmethacrylate treated surface and separated by a spacer with 16 um thickness. After polymerization by exposure to UV light for 10 min the hydrophobically treated glass slide is removed, leaving a HEMA:

PEGMA hydrogel film covalently attached to the remaining glass slide and comprising covalently incorporated FCCC fluoroionophore.

C: Optical Overcoat

Optionally, the optical overcoat as described in Example 2 is applied over the HEMA:PEGMA hydrogel film according to procedure of Example 2.

Example 5

Preparation of Sensing Elements Using Plasticized PVC Polymer

A: Preparation of Sensing Beads

Microscopic beads based on 30 wt. % of poly(vinyl chloride), PVC and 70 wt. % of bis(ethylhexyl)sebacate, BEHS are prepared using a spray dry method. A THF solution containing 1 wt. % PVC and 1 wt. % of BEHS is sprayed with a nebulizer under heated air stream from a heat gun and PVC/BEHS particles (2.5±1 um in diameter) are collected in a cyclone chamber.

50 mg of BEHS solution containing 0.5 mg of hydrogen ion selective chromoionophore III, 1.6 mg of NaHFPB and 22.3 mg of sodium ionophore, bis(12-crown-4) are added to 300 mg of the PVC/BEHS beads and thoroughly mixed, to form $Na^+$/pH sensing microscopic beads.

50 mg of BEHS, 0.5 mg of hydrogen ion sensitive chromoionophore III, 1.6 mg of NaHFPB and 6.3 mg of potassium ionophore III (BME-44) are dissolved in 0.5 ml of 1,1-dichloromethane (DCM). The resulting solution is allowed to stand for 5 hours to evaporate the DCM. Into this cocktail, 300 mg of PVC/BEHS microscopic beads are added and then thoroughly mixed to form $K^+$/pH sensing microscopic beads.

50 mg of BEHS solution is added to 300 mg of the PVC/BEHS beads and thoroughly mixed to form optical white reference beads.

B: Suspension of Beads in Hydrogel

For both sensing and optical reference beads, to prevent conglomerating of the sensing beads, the beads are suspended and fixed in a hydrogel matrix. Two milligrams of the sensing or reference beads are well mixed with 1 mg of PEG and 1 mg of aqueous monomer solution containing 30 wt. % of acrylamide, 1 wt. % of N,N'-methylene-bis-acrylamide and 0.5 wt. % of photoinitiator, Irgacure 2959. The suspension is placed in between two slide glasses and then photopolymerized upon UV light irradiation for 15 min.

C: Fabrication of a polyHEMA-Based Sensor Body

HEMA (2-hydroxyethyl methacrylate) based sensor bodies are prepared by making a polymer plate using a photopolymerization method applied to the monomer solution in between two slide glasses separated by a spacer. To prevent strong adhesion of the resulting polymer to the glass surface, surface modified slide glasses with octadecylsilane are used. The slides (25×75×1 mm) are cleaned in a 1N $HNO_3$ solution at 70° C. for 2 hours and after cooling they were rinsed with milliQ water. After drying in an oven, cleaned slide glasses are placed into 1 L of toluene with 1.5 g of octadecyltrichlorosilane and heated under reflux for 6 hours. The thus surface modified slide glasses are washed by ethanol and milliQ water, and used as substrates for photopolymerization.

A solution of 80 wt. % HEMA, 8.0 wt. % PEGMA (poly (ethylene glycol) methacrylate), 2.0 wt. % DEGDMA (di (ethylene glycol)dimethacrylate), 9.8 wt. % deionized water and 0.2 wt. % Irgacure 651 are transferred into a mold consisting of two surface modified slide glasses separated by a spacer with 400 um thickness. The solution is polymerized to form a crosslinked hydrogel by exposure to low intensity 365 nm UV light (ca 2 $mW/cm^2$) for 10 min. After polymerization, the thus prepared polyHEMA film is removed from the mold. To prepare wells in the polyHEMA film for each sensing capsule, an excimer laser is used with a mask made of a brass plate 200 um thick in which four holes 1 mm in diameter are linearly aligned with 1.3 mm distances in between holes to create sensor compartments in a single sensor body. After successful laser drilling, the polyHEMA film with wells is washed with deionized water.

D: Fabrication of Sensor Window Membrane

To prepare the sensor window membrane, a solution of 32.9 wt. % HEMA, 16.9 wt. % PEGMA, 50 wt. % deionized water and 0.2 wt. % Irgacure 651 is put into a mold consisting of two slide glasses having hydrophobic surfaces separated by a spacer with 16 um thickness. After polymerization by exposure to UV light for 12 min, one of the slide glasses in the mold is carefully removed. In this case, the polyHEMA window membrane with 16 um thickness remains on the surface of another slide glass.

E. Construction of Sensor Body with Wells

To adhere the sensor body with the window membrane, 10 uL of the above mentioned monomer solution is applied to the surface of the thus prepared window membrane on the slide glass and spread. The sensor body is then placed on the window membrane, covered with a slide glass and clamped with binder clips. By exposure to UV light for 15 min, the polyHEMA-based sensor body containing wells with sealed bottoms is successfully prepared.

F. Filling the Sensor Wells and Completing Construction of the Sensor

The thus prepared sensor body is placed on a slide glass with sealed bottoms down and fixed with Scotch tape at the edges of the sensor body. In the respective sensor compartments $Na^+$/pH sensing beads, $K^+$/pH sensing beads and optical white beads for a sensor body with three wells are stuffed by using a tiny glass rod under a stereo microscope.

Another piece of window membrane on a slide glass with hydrophobic surface is then prepared by using the same method mentioned above. Ten uL of the monomer solution mentioned above is applied on the surface of the window membrane and then spread. After removing the tape, the sensor body stuffed with beads on the slide glass is covered with the thus prepared window membrane together with the slide glass and cramped with binder clips. By exposure to UV light for 15 min, all wells with beads in the sensor body are sealed with another window membrane. At this point the sensors are ready for testing.

G. Optical Response of $K^+$ Sensor

Reflectance spectra of the optical $K^+$ sensor in Tris/HCl buffer at pH 7.4 are measured using an a fiber optic spectrometer (e.g. BIF400 UV-VIS, Ocean Optics, CA). As potassium ion concentration increases over the range of 0 mM to 10 mM K+, reflectance at 505 nm (corresponding to the acidic form of chromoionophore III) decreases while the reflectance at 580 nm (corresponding to the basic form of chromoionophore III) increases. The white beads can be used as an optical reference for these measurements. Optionally, the ratio of the 505 and 580 nm reflectances can be used in calculating the potassium ion concentration.

Alternatively, optical characterization of the films can be done via fluorescence spectroscopy. When the film comes in contact with potassium ions, the release of protons from the film leads to a measurable change in it fluorescence properties. Emission peaks are observed at 647 nm and 683 nm. The former corresponds to the protonated form of chromoionophore III, while the latter corresponds to the deprotonated form. When the concentration of $K^+$ in the sample increases, the protonated peak at 647 nm decreases and the deprotonated peak at 683 nm increases. It has been reported that ratiometric analysis can minimize the effects of photobleaching and variations in lamp intensity. Therefore the intensity ratio of the two peaks (647 and 683 nm) is used instead of the absolute fluorescence.

H. Sensor Constructions

Precision coatable sensor constructions based on above described sensor beads are fabricated. The process includes (1) mixing acrylamide and bis-acrylamide monomers and polyethylene glycol oligomers with sensor beads or sensing dyes and a thermal or photo-chemical curing agent (2) coating the mixture onto a sensor backing (3) initiating cure to promote formation of a hydrogel and adhesion of the hydrogel to wells on the sensor backing (4) formation and adhesion of a HEMA window membrane to the resulting hydrogel compositions.

A multi-layer laminate sensor can be fabricated. The process includes (1) cellulose acetate membrane optionally impregnated with thermal or photo-cross linked HEMA polymers as the window membrane (2) a partitioned spacer layer bonded to the dialysis membrane and comprising void spaces filled with the sensor bead (3) an optical window bonded to the partitioned spacer layer.

What is claimed is:

1. An implantable medical device comprising:

a cardiac rhythm management system comprising an implantable pulse generator comprising a power source, circuitry for delivering at least one of cardiac pacing and cardiac shock therapy; and an implantable housing configured to encapsulate the circuitry for delivering at least one of cardiac pacing and cardiac shock therapy; and a chronically implantable chemical sensor in communication with the pulse generator, the chemical sensor configured to detect an ion concentration in a bodily fluid, the chemical sensor comprising:

an optical sensing element selective for potassium ion comprising a polymeric matrix permeable to sodium ions, potassium ions, and hydronium ions;

an optical excitation assembly configured to illuminate the optical sensing element;

an optical detection assembly configured to receive light from the optical sensing element, and an opaque cover layer disposed over a side of the sensing element.

2. The implantable medical device of claim 1, the polymeric matrix comprising a polymer selected from the group consisting of cellulose, polyvinyl alcohol, dextran, polyurethanes, quaternized polystyrenes, sulfonated polystyrenes, polyacrylamides, polyhydroxyalkyl acrylates, polyvinyl pyrrolidones, polyamides, polyesters, and mixtures and copolymers thereof.

3. The implantable medical device of claim 1, the optical sensing element having a first side and a second side, the first side opposite the second side, the optical excitation assembly and the optical detection assembly both disposed on the first side.

4. The implantable medical device of claim 1, the chemical sensor comprising a communication interface configured to communicate wirelessly with the pulse generator.

5. The implantable medical device of claim 1, the chemical sensor comprising a communication interface configured to communicate with the pulse generator via a radio frequency link, an ultrasonic link, or an acoustic link.

6. The implantable medical device of claim 1, the chemical sensor electrically or optically coupled to the pulse generator.

7. The implantable medical device of claim 1, the chemical sensor further configured to detect an ion selected from the group consisting of sodium, chloride, calcium, magnesium, lithium and hydronium.

8. The implantable medical device of claim 7, the optical sensing element comprising an ion selective complexing moiety and a fluorescing moiety, the fluorescing moiety exhibiting differential fluorescent intensity based upon selective binding of an ion to the ion selective complexing moiety.

9. The implantable medical device of claim 8, the ion selective complexing moiety selected from the group consisting of cryptands, crown ethers, bis-crown ethers, calixarenes, noncyclic amides, and hemispherands.

10. The implantable medical device of claim 8, the optical sensing element comprising a fluoroionophore selected from the group consisting of lithium specific fluoroionophores, sodium specific fluoroionophores, and potassium specific fluoroionophores.

11. The implantable medical device of claim 7, the optical sensing element comprising an ion selective complexing moiety and a colorimetric moiety, the colorimetric moiety exhibiting differential light absorbance on selective binding of an ion to the ion selective complexing moiety.

12. The implantable medical device of claim 11, the complexing moiety selected from the group consisting of cryptands, crown ethers, bis-crown ethers, calixarenes, noncyclic amides, and hemispherands.

13. The implantable medical device of claim 7, the optical sensing element comprising an ionophore selected from the group consisting of sodium specific ionophores, potassium specific ionophores, calcium specific ionophores, magnesium specific ionophores, and lithium specific ionophores.

14. The implantable medical device of claim 1, the optical sensing element configured to fluorescently emit light at two different wavelengths.

15. The implantable medical device of claim 1, the bodily fluid selected from the group consisting of blood, interstitial fluid, serum, lymph, and serous fluid.

16. The implantable medical device of claim 1, the excitation assembly comprising a light source, the light source comprising a light emitting diode.

17. The implantable medical device of claim 1, the excitation assembly comprising a first light emitting diode; and a second light emitting diode; the first and second light emitting diodes configured to emit light at different wavelengths.

18. The implantable medical device of claim 1, the detection assembly comprising a component selected from the group consisting of a photodiode, a charge-coupled device (CCD), a junction field effect transistor (JFET) optical sensor, and a complementary metal-oxide semiconductor (CMOS) optical sensor.

19. The implantable medical device of claim 1, the chemical sensor coupled to the implantable housing.

20. The implantable medical device of claim 19, the implantable housing defining an aperture occluded by a transparent member, the optical sensing element in optical communication with the excitation assembly and the detection assembly through the transparent member.

21. The implantable medical device of claim 1, further comprising:

a cardiac pacing lead; and a device header coupled to the implantable housing, the device header configured to provide an electrical connection between the cardiac pacing lead and the pulse generator;

the chemical sensor coupled to the device header.

22. The implantable medical device of claim 1, further comprising:

a cardiac pacing lead, the chemical sensor coupled to the cardiac pacing lead.

23. The implantable medical device of claim 1, the cardiac rhythm management system comprising one of a pacemaker, a cardiac resynchronization therapy (CRT) device, a remodeling control therapy (RCT) device, a cardioverter/defibrillator, a pacemaker-cardioverter/defibrillator, and a hemodynamic monitor.

24. The implantable medical device of claim 1, the chemical sensor further configured to selectively detect a physiological analyte selected from the group consisting of glucose, creatinine, lactate, urea, brain-neural peptide (BNP), nitric-oxide, and troponin.

25. The implantable medical device of claim 1, the chemical sensor further configured to selectively detect a concentration of a physiological analyte indicative of renal function.

26. The implantable medical device of claim 1, further comprising a telemetry circuit.

27. The implantable medical device of claim 1, the chemical sensor further configured to selectively detect a concentration of at least one of creatinine and urea.

28. An implantable cardiac rhythm management system comprising:

a pulse generator comprising circuitry for delivering at least one of cardiac pacing and cardiac shock therapy; and a chronically implantable optical chemical sensor in communication with the pulse generator, the chemical sensor configured to detect an analyte concentration in a bodily fluid, the chemical sensor comprising:

an optical sensing element specific for potassium ion comprising a plurality of beads;

an optical excitation assembly configured to illuminate the optical sensing element; and an optical detection assembly configured to receive light from the optical sensing element.

* * * * *